(12) United States Patent
Guenther et al.

(10) Patent No.: US 10,316,371 B2
(45) Date of Patent: Jun. 11, 2019

(54) **SCREENING METHODS FOR IDENTIFYING SPECIFIC *STAPHYLOCOCCUS AUREUS* INHIBITORS**

(75) Inventors: Richard H. Guenther, Cary, NC (US); Samuel P. Yenne, Raleigh, NC (US); Jerzy R. Szewczyk, Chapel Hill, NC (US)

(73) Assignee: TRANA DISCOVERY, INC., Cary, NC (US)

( * ) Notice: Subject to any disclaimer, the term of this patent is extended or adjusted under 35 U.S.C. 154(b) by 31 days.

(21) Appl. No.: 14/008,960

(22) PCT Filed: Mar. 29, 2012

(86) PCT No.: PCT/US2012/031078
§ 371 (c)(1),
(2), (4) Date: Jan. 14, 2014

(87) PCT Pub. No.: WO2012/135416
PCT Pub. Date: Oct. 4, 2012

(65) Prior Publication Data
US 2014/0163037 A1    Jun. 12, 2014

Related U.S. Application Data

(60) Provisional application No. 61/469,053, filed on Mar. 29, 2011.

(51) Int. Cl.
| | | |
|---|---|---|
| *C12Q 1/6897* | (2018.01) | |
| *A61K 31/137* | (2006.01) | |
| *C07H 21/02* | (2006.01) | |
| *C12N 1/36* | (2006.01) | |
| *C12Q 1/689* | (2018.01) | |
| *A61K 31/192* | (2006.01) | |
| *A61K 31/352* | (2006.01) | |
| *A61K 31/424* | (2006.01) | |
| *A61K 31/433* | (2006.01) | |
| *A61K 31/4439* | (2006.01) | |
| *A61K 31/4545* | (2006.01) | |
| *A61K 31/4738* | (2006.01) | |
| *A61K 31/496* | (2006.01) | |
| *A61K 31/506* | (2006.01) | |
| *A61K 31/517* | (2006.01) | |
| *A61K 31/519* | (2006.01) | |
| *A61K 31/5377* | (2006.01) | |
| *A61K 31/55* | (2006.01) | |

(52) U.S. Cl.
CPC .......... *C12Q 1/6897* (2013.01); *A61K 31/137* (2013.01); *A61K 31/192* (2013.01); *A61K 31/352* (2013.01); *A61K 31/424* (2013.01); *A61K 31/433* (2013.01); *A61K 31/4439* (2013.01); *A61K 31/4545* (2013.01); *A61K 31/4738* (2013.01); *A61K 31/496* (2013.01); *A61K 31/506* (2013.01); *A61K 31/517* (2013.01); *A61K 31/519* (2013.01); *A61K 31/5377* (2013.01); *A61K 31/55* (2013.01); *C07H 21/02* (2013.01); *C12N 1/36* (2013.01); *C12Q 1/689* (2013.01); *C12Q 2600/136* (2013.01)

(58) Field of Classification Search
CPC ............................ C12Q 1/6897; A61K 31/137
USPC ..................................................... 514/252.17
See application file for complete search history.

(56) References Cited

U.S. PATENT DOCUMENTS

| | | | | |
|---|---|---|---|---|
| 3,973,021 | A * | 8/1976 | Horn | A23K 20/116 514/266.24 |
| 2007/0197509 | A1* | 8/2007 | Babinski | A61K 31/47 514/219 |
| 2008/0027044 | A1* | 1/2008 | Lewis | A61K 31/17 514/223.8 |
| 2009/0270423 | A1 | 10/2009 | Blackwell et al. | |
| 2010/0016333 | A1* | 1/2010 | Flanner | A61K 9/1635 514/254.11 |

FOREIGN PATENT DOCUMENTS

| | | |
|---|---|---|
| WO | 2010036795 A2 | 4/2010 |
| WO | 2010136804 A1 | 12/2010 |
| WO | WO 2010 136804 | * 12/2010 |

OTHER PUBLICATIONS

Menestrina et al. (J. Membrane Biol., (1986), vol. 90, pp. 177-190) (Year: 1986).*

(Continued)

*Primary Examiner* — Brandon J Fetterolf
*Assistant Examiner* — Taina D Matos Negron
(74) *Attorney, Agent, or Firm* — Hunton Andrews Kurth LLP; David Bradin

(57) ABSTRACT

Methods of inhibiting *S. aureus* propagation, and screening for compounds that inhibit *S. aureus* propagation, are described. A method of inhibiting *S. aureus* propagation comprises either inhibiting or stabilizing ribosomal binding of a specific *S. aureus* tRNA in the *S. aureus* by an amount sufficient to inhibit *S. aureus* protein expression. A method of screening for compounds useful for inhibiting *S. aureus* propagation comprises contacting a specific *S. aureus* tRNA to a ribosome that binds that tRNA in the presence of the test compound and an mRNA that codes for methionine and arginine (i.e., includes the sequence AUGAGA), and then determining whether the compound inhibits the binding of that tRNA.

3 Claims, 14 Drawing Sheets
Specification includes a Sequence Listing.

(56) References Cited

OTHER PUBLICATIONS

King, Pei-Pei et al.; "Structure-Activity Relationships of Novel 2-Substituted Quinazoline Antibacterial Agents", Journal of Medicinal Chemistry, American Chemical Society, US, vol. 42, No. 22, Nov. 4, 1999, pp. 4705-4713.
Cheng, TJR et al.; "High-throughput identification of antibacterials against methicillin-resistant *Staphylococcus aureus* (MRSA) and the transflycosylase"; Bioorganic & Medicinal Chemistry, Pergamon, GB, vol. 18, No. 24, Dec. 15, 2010, pp. 8512-8529.
Studer, Sean M. et al. "Binding of mRNA to the Bacterial Translation Initiation Complex", Methods of Enzymology, 2007, vol. 430, pp. 31-44.
Spirin, A.S., Biosintez belka: initsiatsiya tanslyatsii, Sorosovskiy obrazovatelny zhurnal, 1999, No. 5, pp. 2-7.
International Search Report of PCT Patent Application No. PCT/US2012/031078 dated Mar. 29, 2012.
European Search Report of European Patent Application No. 12764343.5 dated Nov. 20, 2014.
Studer, Sean M. et al., "Binding of mRNA to the Bacterial Translation Initiation Complex", Methods in Enzymology, vol. 430, 2007, pp. 31-44, XP055093503.
Harris, N. et al., "Antifolate and antibacterial activities of 6-substituted 2, 4-diaminoguinazolines", European Journal of Medicinal Chemistry, Editions Scientifique Elsevier, Paris, FR, vol. 27, No. 1, Jan. 1, 1992 (Jan. 1, 1992), pp. 7-18.

\* cited by examiner

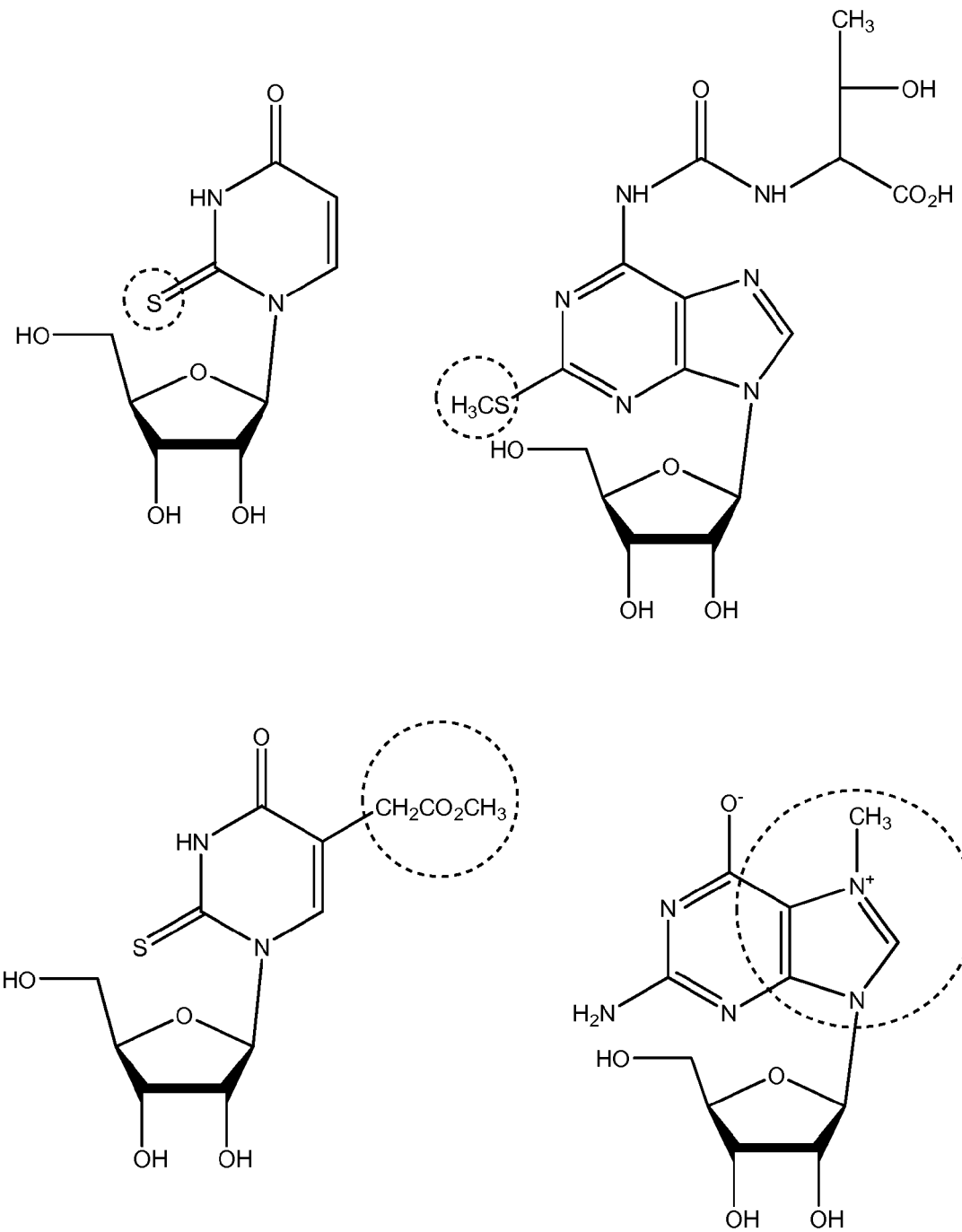
FIG. 3, Cont'd

```
          A      U      *Fluorescein
          U      A
          G      C
          G      C
          C      G
      s2C            A
    U                   t6A
       mnm5U C U
```

FIG. 4

A  Base protection of mnm⁵s²U

B  Base protection of m²A

C  Modification of adenosine to t6A

D  Generalized sugar protection and phosphitylation of modified nucleotides

Complex dissociation over time/Mg 20 represents buffer control.

SEQUENCE LISTING

```
<160> NUMBER OF SEQ ID NOS: 4

<210> SEQ ID NO 1
<211> LENGTH: 18
<212> TYPE: RNA
<213> ORGANISM: Artificial
<220> FEATURE:
<223> OTHER INFORMATION: Artificial sequence including the minimal mRNA
      sequence that includes the  Shine-Delgarno (S-D) sequence, the
      "box" sequence, the AUG sequence encoding methionine, and the S.
      aureus-specific triplet codon encoding arginine

<400> SEQUENCE: 1
aggagauaau aaaugaga                                                 18

<210> SEQ ID NO 2
<211> LENGTH: 54
<212> TYPE: RNA
<213> ORGANISM: Artificial
<220> FEATURE:
<223> OTHER INFORMATION: Artificial sequence including the minimal mRNA
      sequence that includes the  S-D sequence, the "box" sequence, the
      AUG sequence encoding methionine, and the S. aureus-specific
      triplet codon encoding arginine, plus additional bases to
      stabilize the mRNA

<400> SEQUENCE: 2
gggcgauaac acucaggaga uaauaaauga gaacagcuga ucaaucgugc aucc          54

<210> SEQ ID NO 3
<211> LENGTH: 17
<212> TYPE: RNA
<213> ORGANISM: S. aureus
<220> FEATURE:
<221> NAME/KEY: misc_feature
<222> LOCATION: (6)..(6)
<223> OTHER INFORMATION: n is 2-thiocytidine
<220> FEATURE:
<221> NAME/KEY: misc_feature
<222> LOCATION: (8)..(8)
<223> OTHER INFORMATION: n is 5-methylaminomethyluridine
<220> FEATURE:
<221> NAME/KEY: misc_feature
```

```
<222> LOCATION: (11)..(11)
<223> OTHER INFORMATION: n is N6-threonylcarbamoyladenosine

<400> SEQUENCE: 3
auggcnuncu nagccau                                                17

<210> SEQ ID NO 4
<211> LENGTH: 71
<212> TYPE: DNA
<213> ORGANISM: Artificial
<220> FEATURE:
<223> OTHER INFORMATION: Single stranded DNA template used to prepare
      mRNA

<400> SEQUENCE: 4
ggatgcacga ttgatcagct gttctcattt attatctcct gagtgttatc gccctatagt    60
gagtcgtatt a                                                        71
```

SCREENING METHODS FOR IDENTIFYING SPECIFIC *STAPHYLOCOCCUS AUREUS* INHIBITORS

CROSS-REFERENCE TO RELATED APPLICATIONS

This application is a U.S. national phase under the provisions of 35 U.S.C. § 371 of International Patent Application No. PCT/US12/31078 filed Mar. 29, 2012, which in turn claims the benefit of U.S. Provisional Patent Application No. 61/469,053 filed Mar. 29, 2011. The disclosures of such international patent application and U.S. provisional priority patent application are hereby incorporated herein by reference in their respective entireties, for all purposes.

FIELD OF THE INVENTION

The present invention concerns antibacterial agents that are directed against tRNA targets, particularly, tRNA targets specific for *Staphylococcus aureus*, and methods of screening for antibacterial and agents directed against such tRNA targets.

BACKGROUND OF THE INVENTION

The need to discover new classes of antibiotic compounds and/or antibiotics with different target sites is being reiterated frequently with the threat of drug resistant pathogens, reemerging pathogens and/or bio-terrorism concerns. With each passing decade, strains of virtually all important bacterial pathogens of humans have arisen that are resistant to at least one class of antibiotics, and strains resistant to multiple classes of antibiotics have become increasingly widespread. In fact, according to the Centers for Disease Control and Prevention (CDC 2000-2001), virtually all significant bacterial infections in the world are becoming resistant to the antibiotic treatment of choice. This rise is generally attributed to pathogens which have become resistant to commonly used antibiotics which focus on a limited number of target sites. Some pathogens that were generally considered historical disease causing agents are reemerging either due to genetic modifications making the organism more virulent and/or exposure to a larger portion of the world population. Related to the naturally occurring genetic modifications are intentional genetic modifications conducted by groups with bio-terrorist desires. Frequently, these intentional genetic modifications will focus on making an otherwise susceptible disease pathogen resistant to the current antibiotics with known target sites.

For *Staphylococcus aureus* in particular, evolving resistance mechanisms have created significant treatment challenges over the years. Beginning with penicillinase-producing strains that were resistant to conventional penicillins, the need for newer, effective antibiotics against this organism has ensued. Most recently, with the emergence of community-associated methicillin-resistant *S. aureus* (CA-MRSA), traditional first-line antibiotics are once again ineffective, and, unfortunately, the prevalence of CA-MRSA is already high, accounting for well over 60% of all cases of community-associated *S. aureus* infections. Even worse is the recent discovery of multi-drug resistant strains of CA-MRSA that are capable of rapidly acquiring resistance to most all available agents via a plasmid-mediated mechanism. In the face of this threat, a number of new antibiotics targeted against *S. aureus* are under development. However, of the new antibiotics known to be in clinical development, none has a novel mechanism of action. For these reasons the need for totally new treatments for *S. aureus* infections is evident.

It would be advantageous to have a method for identifying compounds useful for treating *S. aureus* infections via a new mechanism. The present provides such a method, as well as treatment methods using the discovered compounds.

SUMMARY OF THE INVENTION

Methods for identifying specific inhibitors of *S. aureus*, isolated tRNA fragments that are useful in these methods, and kits including these fragments, are disclosed. Also disclosed are methods of treating and/or preventing *S. aureus* infection using the inhibitors of *S. aureus* propagation, and pharmaceutical compositions including the inhibitors and a pharmaceutically-acceptable carrier. Combination therapy using one or more of the inhibitors, and a second anti-bacterial compound, are also disclosed.

The inhibition of *S. aureus* propagation results from inhibition of *S. aureus* protein synthesis. In one embodiment, inhibition refers to the selective inhibition of *S. aureus* in the presence of other bacteria. One advantage of selective inhibition of *S. aureus* is that, in this manner, one can treat bacterial infections without the concomitant development of antibacterial resistance in the colon, and the side effects resulting from disturbing beneficial bacteria in the colon, such as diarrhea, CDAD, pseudomembranous colitis, and the like.

In one embodiment, the methods for screening inhibitors of *S. aureus* propagation involve forming a mixture comprising a sequence of a tRNA anticodon stem loop fragment, a programmed ribosome capable of binding to the tRNA anticodon stem loop fragment, and a test compound. The programmed ribosome includes an mRNA oligomer, fMet, and the ribosome.

The mixture is incubated under conditions that allow binding of the tRNA anticodon stem loop fragment and the programmed mRNA to the bacterial ribosome in the absence of the test compound. One can then determine whether or not a test compound inhibits the propagation of *S. aureus*. A compound that interferes with the binding of the tRNA ASL fragment (i.e., inhibits binding, referred to as inhibition, or inhibits release, referred to as agonism) and the ribosome is indicative of the test compound being an inhibitor of *S. aureus* propagation.

*S. aureus* uses six different tRNA to incorporate arginine into a growing protein. Other bacteria use five different tRNA to incorporate arginine into the growing protein. The methods described herein use the tRNA specific for arginine incorporation in *S. aureus* in a screening method, where the tRNA forms a complex. Specific inhibitors of *S. aureus* will interrupt the complex, and therefore prevent arginine incorporation into the growing protein/peptide, which results in bactericidal action. Once inhibitors and/or agonists are identified, they can be tested in vitro for specific *S. aureus* activity, for example, by incubating them with other tRNA/ribosome complexes, to see if they do or do not disrupt these complexes. Alternatively, one can incubate the inhibitors with a variety of bacteria and identifying those specific inhibitors of arginine incorporation which are not bactericidal to other bacteria, for example, beneficial bacteria.

In one embodiment, the anti-codon stem loop ASL$^{Arg}$, a tRNA oligomer with the following sequence is synthesized: 5'-A-U-G-G-C-s$^2$C-U-mnm$^5$U-C-U-t$^6$A-A-G-C-C-A-U-3'. Various labels may be attached to either end to faciliate various assay detection technologies. For the assays described in the working examples, FITC was incorporated during synthesis to the 3'-end. An isolated RNA sequence comprising A-U-G-G-C-s$^2$C-U-mnm$^5$U-C-U-t$^6$A-A-G-C-C-A-U, either by itself, or with up to 100, up to 50, up to 25, up go 20, or up to 15 base pairs on either or both ends, is intended to be within the scope of the invention.

The mRNA oligomer for programming the ribosome has the sequence AGA. The linear sequence of the tRNA anticodon stem loop fragment includes the Shine-Dalgarno (or S-D) sequence, the five to eight nucleotide bases that follow the Shine-Dalgarno sequence, the triplet codon encoding methionine (AUG), which initiates protein translation, and the triplet codon for encoding arginine that is specific for *S. aureus*.

A representative S-D sequence is AGGAG, and a representative "box" sequence following the S-D sequence is AUAAUAA. A minimal mRNA sequence that includes the S-D sequence, the "box" sequence, the AUG sequence encoding methionine, and the *S. aureus*-specific triplet codon encoding arginine (AGA) is provided below:

AGGAGAUAAUAAAUG<u>AGA</u>.

To provide stability, the sequence can include additional bases to the left and right of this sequence. A representative sequence is shown below:

5'-GGGCGAUAACACUCAGGAGAUAAUAAAUG<u>AGA</u>ACAGCUGAUCAAUC

GUGCAUCC-3'

While other triplet codons can be present before the arginine codon, such would unnecessarily complicate the assay, as one would need to actually translate the intermediate amino acids before arriving at a complex between the ribosome and the ASL$^{Arg}$, which would by necessity include other components in the assay. Additional nucleotides can be present after the ASL$^{Arg}$, and it is actually preferred that such be present, to stabilize the oligonucleotide, even though they will not actually be used to produce a peptide strand, since translation will, ideally, be stopped at the first Arg.

There are two main approaches described herein for inhibiting protein synthesis in *Staphylococcus aureus*. One is to destabilize the complex formed between the ribosome and the ASL$^{Arg}$, so that the arginine is never added to the protein fragment being transcribed. The other is to overly stabilize the complex, so that translation never proceeds any further. That is, if protein production is inhibited by either blocking the release of the protein fragment from the ribosome, or preventing the addition of arginine to the protein fragment, the bacteria is destroyed. If the protein fragment is not released then, further amino acids are not added to the growing peptide chain, and the bacteria is destroyed. Both types of anti-bacterial agents are intended to be within the scope of the invention described herein.

The ribosome can be an *S. aureus* ribosome, an *E. coli* ribosome, or any other suitable bacterial ribosome that allows one to form the desired complex, which is then either stabilized or destabilized by the active compounds described herein.

In *E. coli*, the mRNA consensus sequence 5' AGGAGGU 3' is between 5 and 8 bases upstream from the AUG translation initiation codon (i.e., the codon for methionine). The S-D sequence forms complementary base pairs with a consensus sequence found at the 3' end of the 16S rRNA molecule (q.v.) in the 30S subunit of the ribosome. The S-D sequence thus serves as the binding site for bacterial mRNA molecules on ribosomes.

In one embodiment, the screening assay involves the further step of screening active compounds for their ability to inhibit the propagation of bacteria other than *S. aureus*, and which use a different ASL for arginine than *S. aureus*. This is indicative of compounds that inhibit or stabilize the formation of a complex between the ribosome and the Shine-Delgarno sequence. Where the compounds have broad spectrum antimicrobial activity, and inhibit the formation of a complex between the ribosome and the Shine-Delgarno sequence, the compounds demonstrate a heretofore unknown mechanism of action. Such compounds, and a method of treating bacterial infections using such compounds, are intended to be within the scope of the invention described herein.

Kits for screening inhibitors of the various processes described above are also disclosed. The kits comprise a nucleic acid molecule consisting essentially of a linear sequence of a tRNA anticodon stem loop fragment; and a detectable label.

Compounds which are inhibitors of the various processes described above can be used in methods of treating and/or preventing an *S. aureus* infection. That is, compounds which destabilize or stabilize the complex formed between the mRNA, and the ribosome during translation of the codon for arginine that is specific to *S. aureus*, AGA, can inhibit bacterial protein formation. Such methods are also within the scope of the invention.

Pharmaceutical compositions useful in these methods are also within the scope of the invention. Such pharmaceutical compositions include one or more inhibitors, as described herein, and a pharmaceutically-acceptable carrier. Combination therapy, using additional antibacterial compounds which function by a different mechanism, is also disclosed.

The foregoing and other objects and aspects of the present invention are explained in detail in the drawings herein and the specification set forth below.

BRIEF DESCRIPTION OF THE DRAWINGS

FIG. 4 is an illustration of a synthetic oligomer representing the anticodon stem loop from tRNA$^{Arg}$ in *S. aureus*. Only when the modifications are present will the ASL bind to programmed ribosomes, which binding can be detected by monitoring the change in fluorescence. Although the label in this figure is a fluorescent label, other labels can be used to facilitate detection.

FIG. 13 is a chart showing the result of time-kill experimental results, over a twenty four hour time period, on control (black square), vancomycin at two times its minimum inhibitory concentration (MIC) value (green diamonds), vancomycin at four times its MIC (green circles), Compound #880 at two times its MIC (red circles), Compound #880 at four times its MIC (red squares), Compound #169 at two times its MIC (blue triangles), and Compound #169 at four times its MIC (upside down blue triangles), shown in terms of bacterial counts ($Log_{10}$ cFu/ml) over time (hours).

DETAILED DESCRIPTION

Figure 1:
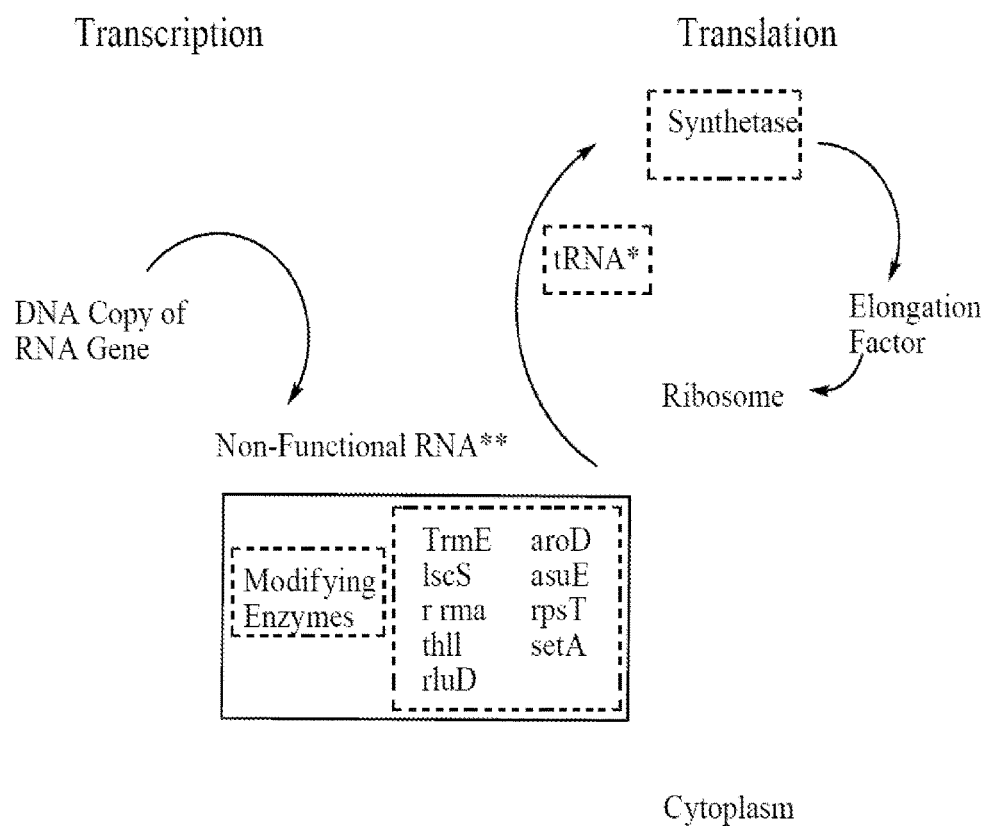
FIG. 1 is a graphic illustration showing the synthesis of proteins via the processes of transcription and translation.

The present invention relates to compositions and methods for identifying compounds useful for specifically inhibiting S. aureus propagation, as well as pharmaceutical compositions and methods for treating S. aureus infections by inhibiting S. aureus propagation. S. aureus propagation can be inhibited by inhibiting translation of S. aureus RNA into proteins. The inhibition can be achieved by either inhibiting or stabilizing the complex formed between the bacterial ribosome and the codon specific for S. aureus for arginine, AGA. Either approach inhibits the ability of the bacteria to produce proteins.

In one embodiment, the screening assay involves the further step of screening active compounds for their ability to inhibit the propagation of bacteria other than S. aureus, and which use a different ASL for arginine than S. aureus. This is indicative of compounds that inhibit or stabilize the formation of a complex between the ribosome and the Shine-Delgarno sequence. Where the compounds have broad spectrum antimicrobial activity, and inhibit the formation of a complex between the ribosome and the Shine-Delgarno sequence, the compounds demonstrate a heretofore unknown mechanism of action. Such compounds, and a method of treating bacterial infections using such compounds, are intended to be within the scope of the invention described herein.

Prior to describing this invention in further detail, however, the following terms will first be defined.

Definitions

As used herein, an "inhibitor" refers to any compound capable of preventing, reducing, or restricting S. aureus propagation. An inhibitor may inhibit S. aureus propagation, for example, by preventing, reducing or restricting S. aureus protein formation, specifically by inhibiting arginine incorporation into a growing protein strand, and, more specifically, by inhibiting arginine incorporation by focusing on a) disrupting or b) stabilizing a complex formed by a tRNA specific for S. aureus' incorporation of arginine into a growing protein strand. In some embodiments, the inhibition is at least 20% (e.g., at least 50%, 70%, 80%, 90%, 95%, 98%, 99%, 99.5%) of the S. aureus propagation as compared to the propagation in the absence of the inhibitor. In one aspect, an inhibitor prevents, reduces, or restricts the binding of a tRNA, or fragment thereof, to a ribosome, preferably a ribosome associated with protein and peptide synthesis. In another aspect, a stabilizer (agonist) stabilizes the binding of a tRNA, or fragment thereof, to a ribosome, preferably a ribosome associated with protein and peptide synthesis.

More particularly, the binding in the foregoing two aspects is related to the incorporation or arginine into a growing peptide or protein, and, most particularly, the binding is specific for the incorporation of arginine into a protein or peptide encoded by S. aureus, and the tRNA is not useful for the incorporation of arginine into proteins or peptides of other bacteria.

The selection of ASL Arg over ASLs Lys or Glu or Gln reflects an improvement in target selection. A recent analysis of bacterial codon usage including S. aureus (Rocha 2004) has found a high degree of bias. While 6 codons exist for arginine, only two of them are used in high frequency. By designing an assay that selectively looks to inhibit the target tRNA, an added selectivity of the therapeutic can be expected. In addition, a concern in targeting of tRNA Lys function raises the potential for inhibition of human mitochondrial function. The selection of a UCU anticodon as the therapeutic target has an advantage in that it eliminates that concern in that in human mitochondria, the AGA codon is not an amino acid encoding triplet, but rather a stop codon (Kirino 2005).

As used herein, a "label" or "detectable label" is any composition that is detectable, either directly or indirectly, for example, by spectroscopic, photochemical, biochemical, immunochemical, or chemical means. Useful labels include, but are not limited to, radioactive isotopes (for example, $^{32}$P, $^{35}$S, and $^{3}$H), dyes, fluorescent dyes (for example, Cy5 and Cy3), fluorophores (for example, fluorescein), electron-dense reagents, enzymes and their substrates (for example, as commonly used in enzyme-linked immunoassays, such as, alkaline phosphatase and horse radish peroxidase), biotin-streptavidin, digoxigenin, or hapten; and proteins for which antisera or monoclonal antibodies are available. Moreover, a label or detectable moiety can include an "affinity tag" that, when coupled with the target nucleic acid and incubated with a test compound or compound library, allows for the affinity capture of the target nucleic acid along with molecules bound to the target nucleic acid. One skilled in the art will appreciate that an affinity tag bound to the target nucleic acid has, by definition, a complimentary ligand coupled to a solid support that allows for its capture. For example, useful affinity tags and complimentary partners include, but are not limited to, biotin-streptavidin, complimentary nucleic acid fragments (for example, oligo dT-oligo dA, oligo T-oligo A, oligo dG-oligo dC, oligo G-oligo C), aptamers, or haptens and proteins for which antisera or monoclonal antibodies are available. The label or detectable moiety is typically bound, either covalently, through a linker or chemical bound, or through ionic, van der Waals or hydrogen bonds to the molecule to be detected.

The term "host" as used herein refers to human or animal cells or tissues in vitro and human or animal subjects (e.g., avian or mammalian cells, tissues and subjects such as chickens, turkeys, mouse, rat, cats, dogs, cows, pigs, horses, etc.).

The term "ribosome" as used herein refers to both intact active ribosomes and ribosome subunits that retain tRNA binding, such as 30S subunits. Specific bacterial ribosomes that can be used in the assay methods described herein include *S. aureus* and *E. coli* ribosomes.

The Shine-Dalgarno (S-D) sequence is a ribosomal binding site in the mRNA, generally located 5-8 basepairs upstream of the start codon AUG, which codes for methionine. To make the initiation site optimal, an optimal Shine-Dalgarno sequence is combined with an optimal distance to the AUG (i.e., 5-8 basepairs).

The Shine-Dalgarno sequence exists only in prokaryotes. The six-base consensus sequence is AGGAGG; in *E. coli*, for example, the sequence is AGGAGGU. In *S. aureus*, the sequence is GGAGGG (East, "Cloning and Sequence Determination of Six *Staphylococcus aureus*/I-Lactamases and Their Expression in *Escherichia coli* and *Staphylococcus aureus*," Journal of General Microbiology, 135, 1001-1015 (1989)). This sequence helps recruit the ribosome to the mRNA to initiate protein synthesis by aligning it with the start codon. The complementary sequence (CCUCCU), is called the anti-Shine-Dalgarno sequence and is located at the 3' end of the 16S rRNA in the ribosome. The eukaryotic equivalent of the Shine-Dalgarno sequence is called the Kozak sequence.

Mutations in the Shine-Dalgarno sequence can reduce translation. This reduction is due to a reduced mRNA-ribosome pairing efficiency, as evidenced by the fact that complementary mutations in the anti-Shine-Dalgarno sequence can restore translation. Accordingly, it is preferred that the Shine-Dalgarno sequence be appropriately matched with the ribosome that is used. That is, if a *S. aureus* ribosome is used, then the Shine-Dalgarno sequence should be the sequence used by *S. aureus*. If an *E. coli* ribosome is used, then the Shine-Dalgarno sequence should be the sequence used by *E. coli*.

When the Shine-Dalgarno sequence and the anti-Shine-Dalgarno sequence pair, the translation initiation factors IF2-GTP, IF1, IF3, as well as the initiator tRNA fMet-tRNA (fmet) are recruited to the ribosome. Once the tRNA(fmet) is recruited to the ribosome, the protein translation will begin (starting with methionine).

Since the adjacent codon is the codon for arginine that is specific for *S. aureus*, the complex that is formed is a specific target for inhibition or stabilization. If complex formation is inhibited, then the *S. aureus* bacteria cannot produce proteins, and will thus die. If the complex is stabilized, then the protein sequence terminates at arginine, and cannot proceed further. This also kills *S. aureus*.

As used herein, an "inhibitor" refers to any compound capable of preventing, reducing, or restricting *S. aureus* propagation. An inhibitor may inhibit *S. aureus* propagation, for example, by preventing, reducing or restricting protein (or peptide) translation in a specific manner, i.e., by inhibiting the use of the codon specific for arginine (AGA) that is used by *S. aureus* but not most other bacteria. During protein translation, the mRNA including the AGA codon is present in a ribosome, and the bacterial tRNA (ASL Arg) forms a complex with the mRNA and the ribosome. Compounds that stabilize this complex, or inhibit this complex, are useful in inhibiting the propagation of *S. aureus*.

The terms "alkyl", "aryl" and other groups refer generally to both unsubstituted and substituted groups unless specified to the contrary.

Unless specified otherwise, alkyl groups are hydrocarbon groups and are preferably $C_1$-$C_{15}$ (that is, having 1 to 15 carbon atoms) alkyl groups, which can be branched or unbranched, acyclic or cyclic. The above definition of an alkyl group and other definitions would apply also when the group is a substituent on another group (for example, an alkyl group as a substituent of an alkylamino group or a dialkylamino group).

The term "aryl" refers to any functional group or substituent derived from a simple aromatic ring, such as phenyl, thiophenyl, indoyl, etc. "Arylalkyl" refers to an aryl moiety attached to an alkyl moiety, and "alkaryl" refers to an alkyl moiety attached to an aryl moiety.

The term "alkenyl" refers to a straight or branched chain hydrocarbon group with at least one double bond, preferably with 2-15 carbon atoms.

The term "alkynyl" refers to a straight or branched chain hydrocarbon group with at least one triple bond, preferably with 2-15 carbon atoms.

The terms "alkylene," "alkenylene" and "alkynyllene" refer to bivalent forms of alkyl, alkenyl, and alkynyl groups, respectively.

The terms "halogen" or "halo" refer to fluoro, chloro, bromo, or iodo. Substituent groups building off of the hydrocarbon groups include alkoxy, aryloxy, acyloxy, haloalkyl, perfluoroalkyl, fluorine, chlorine, bromine, carbamoyloxy, hydroxyl, nitro, cyano, cyanoalkyl, azido, azidoalkyl, formyl, hydrazine, hydroxyalkyl, alkoxyalkyl, and the like.

The specific tRNA referred to herein with respect to *S. aureus* tRNA is preferably a unique or unusual tRNA: that is, one that contains one or more modified bases other than adenine, guanine, cytosine, or uracil in the anticodon binding region (including both the stem and loop thereof), and/or preferably a tRNA that is only found in *S. aureus* for binding to a corresponding amino acid (e.g., arginine) during protein translation in *S. aureus*. That is, preferably, the tRNA is specific for arginine, and is only found in *S. aureus*, or at least is not found in the vast majority (i.e., greater than 90%, preferably greater than 95%, and, ideally, greater than 99% of bacteria other than *S. aureus*).

Preferably, the modified base or bases is/are a nucleotide(s) that is/are at a binding site as described below (e.g., nucleotides 27 through 43) and participates in the binding event. Where carried out in vivo, the tRNA for the corresponding amino acid bound by the *S. aureus* tRNA preferably does not have the same modified base at the binding site or corresponding nucleotide in the host organism (i.e., pathogen specific modification). Many of these exist in the human host and in agronomically important animal hosts as set forth above). Examples of modified bases are set forth below.

I. tRNA Fragments Useful in the Methods Described Herein

The tRNA fragments (or "tool tRNA fragments") for use in the screening methods described herein are tRNA fragments from *S. aureus* that code for arginine, and which, in one embodiment, have the formula below:

AUGGCs2CUmnm5UCUt6AAGCCAU-label

In one aspect, the tRNA fragment comprises the nucleic acid sequence AUGGCs2CUmnm5UCUt6AAGCCAU-Fluorescein.

In another aspect, the tRNA fragment above can be modified with one or more modified nucleosides, so long as it maintains its selectivity for arginine, and the modified tRNA is still specific for *S. aureus* over other bacteria. In one aspect, the tRNA fragment incorporates one, two, three, or more modified nucleosides into the nucleic acid sequence. In another aspect, the tRNA fragments incorporate three modified nucleosides into their nucleic acid sequence. Modified nucleosides that can be incorporated into the tRNA fragments include any modified nucleotide, including, but not limited to unknown modified adenosine (?A), 1-methyladenosine (m1A), 2-methyladenosine (m2A), $N^6$-isopentenyladenosine (i6A), 2-methylthio-$N^6$-isopentenyladenosine (ms2i6A), $N^6$-methyladenosine (m6A), $N^6$-threonylcarbamoyladenosine (t6A), $N^6$-methyl-$N^6$ threonylcarbomoyladenosine (m6t6A), 2-methylthio-$N^6$-threonylcarbamoyladenosine (ms2t6A), 2'-O-methyladenosine I Inosine (Am), 1-methylinosine Ar(p) 2'-O-(5-phospho)ribosyladenosine (m1I), $N^6$-(cis-hydroxyisopentenyl)adenosine (io6A), Unknown modified cytidine (?C), 2-thiocytidine (s2C), 2'-O-methylcytidine (Cm), $N^4$-acetylcytidine (ac4C), 5-methylcytidine (m5C), 3-methyl cytidine (m3C), lysidine (k2C), 5-formylcytidin (f5C), 2'-O-methyl-5-formylcytidin (f5Cm), unknown modified guanosine (?G), 2'-O-(5phospho) ribosylguanosine (Gr(p)), 1-methylguanosine (m1G), $N^2$-methylguanosine (m2G), 2'-O-methylguanosine (Gm), $N^2N^2$-dimethylguanosine (m22G), $N^2,N^2,$2'-O-trimethylguanosine (m22Gm), 7-methylguanosine (m7G), archaeosine (fa7d7G), queuosine (Q), mannosyl-queuosine (manQ), galactosyl-queuosine (galQ), wybutosine (yW), peroxywybutosine (02yW), unknown modified uridine (?U), 5-methylaminomethyluridine (mnm5U), 2-thiouridine (s2U), 2'-O-methyluridine (Um), 4-thiouridine (s4U), 5carbamoylmethyluridine (ncm5U), 5-methoxycarbonylmethyluridine (mcm5U), 5methylaminomethyl-2-thiouridine (mnm5s2U), 5-methoxycarbonylmethyl-2-thiouridine (mcm5s2U), uridine 5-oxyacetic acid (cmo5U), 5-methoxyuridine (mo5U), 5carboxymethylaminomethyluridine (cmnm5U), 5-carboxymethylaminomethyl-2-thiouridine (cmnm5s2U), 3-(3-amino-3-carboxypropyl)uridine (acp3U), 5-(carboxyhydroxymethyl)uridinemethyl ester (mchm5U), 5-carboxymethylaminomethyl-2'-O-methyluridine (cmnm5Um), 5-carbamoylmethyl-2'-O-methyluridine (ncm5Um), Dihydrouridine (D), pseudouridine (ψ), 1-methylpseudouridine (m1ψ), 2'-O-methylpseudouridine (ψm), ribosylthymine (m5U), 5-methyl-2-thiouridine (m5s2U), and 5,2'-O-dimethyluridine (m5Um).

The tRNA fragment may also be any length of a fragment from a tRNA. In one aspect, the tRNA fragment comprises a fragment of between 9 to 15 continuous nucleotides of a tRNA, 10 to 14 continuous nucleotides of a tRNA, or between 11 to 13 continuous nucleotides of a tRNA. In another aspect, the fragment is a fragment of 8, 9, 10, 11, 12, 13, 14, 15, or 16 continuous nucleotides of a tRNA. In a further aspect, the fragment is a fragment of 12 continuous nucleotides of a tRNA.

The tRNA fragment may or may not be capable of forming a secondary structure. In a one aspect, the tRNA fragment is not capable of forming a stem loop structure with itself. In another aspect, the fragment is a linear fragment of a tRNA that is not capable of forming a stem loop structure with itself.

The tRNA fragment may also be linked to additional nucleic acids. For example, the tRNA fragment may be linked to one or more additional nucleic acids depending on the assay method. In one aspect, the tRNA fragment may be linked to nucleotides used to attach the fragment to a solid support surface. In another aspect, the fragment tRNA is linked to additional nucleic acid molecules at one or both terminal end of the tRNA fragment. In another aspect, the fragment tRNA is linked to additional nucleic acid molecules at both terminal ends. The additional nucleic acid sequences can be any length, preferably between 8 and 16 nucleotides, between 10 and 14 nucleotides, more preferably 12 nucleotides in length. In one aspect, the terminal sequences do not allow the tRNA fragment to form a secondary structure, such as a hairpin loop structure.

The specific tRNA referred to herein with respect to host tRNA is also preferably a unique or unusual tRNA: that is, one that contains one or more modified bases other than adenine, guanine, cytosine, or uracil in the anticodon binding region (including both the stem and loop thereof), as set forth above, and/or preferably one that is the only tRNA available in that host for binding to RNA for priming of translation of *S. aureus* proteins.

The region of the tRNA to which binding occurs as described herein is, in general, the tRNA anticodon stem-loop structure, and most preferably the loop structure itself. Following conventional tRNA nucleotide numbering (see, e.g., M. Sprinzl et al., Compilation of tRNA sequences and sequences of tRNA genes, Nucleic Acids Res. 26, 148-153 (1998)), the site to which binding occurs is from nucleotide 27 or 32 to nucleotide 39, 41 or 43. Nucleotides 32, 34, 35, 37 and 39 are preferred binding sites, and nucleotides 34 and 37 are particularly preferred binding sites. Binding may be to a single site or combination of sites comprising nucleotides within this range.

As noted above, a method of screening for compounds useful for inhibiting *S. aureus* propagation is disclosed herein. The method involves contacting a specific *S. aureus* tRNA, such as a specific tRNA$^{arg}$, to a ribosome that binds that tRNA in the presence of the test compound. The contacting step is typically carried out in vitro in an aqueous solution, with the tRNA, the ribosome, an appropriate messenger RNA, and the test compound in the aqueous solution. The contacting step may be carried out with a single test compound or with a library of probes or test compounds in any of a variety of combinatorial chemistry systems, as discussed in greater detail below. The appropriate messenger RNA comprises the Shine-Dalgarno sequence appropriate for the ribosome. The ribosome can be, for example, a S. aureus or E. coli ribosome, and each has its own anti-Shine-Dalgarno sequence that interacts with the Shine-Dalgarno sequence. The messenger RNA also comprises a series of 5-8 base pairs to the right of the Shine-Dalgarno sequence, then the codon AUG, which codes for methionine, then the codon AGA, which, specifically in S. aureus codes for arginine. The mRNA can optionally, but preferably, include from 1 to 100 base pairs to the left of the Shine-Dalgarno sequence, and from 1 to 100 base pairs to the right of the AGA codon.

After the contacting step, the next step involves determining whether the compound inhibits the binding of the specific tRNA to the ribosome (e.g., the binding of $tRNA^{arg}$ at the appropriate position(s) on the ribosome for incorporation of an arginine into a growing peptide or protein.

The determining step can be carried out by any suitable means, such as the filter binding assays disclosed below, or in any of the binding detection mechanisms commonly employed with combinatorial libraries of probes or test compounds as discussed below. Inhibition of ribosomal binding by the test compound indicates that the test compound is useful for inhibiting *Staphylococcus aureus* propagation. Compounds identified by this technique are sometimes referred to as "active compounds" herein. The method is particularly useful for identifying compounds that inhibit S. aureus growth, preferably bacteria that contain a single tRNA for a particular amino acid, such as a single arginine tRNA that is specific for S. aureus over other bacteria.

A method of screening for compounds useful for inhibiting S. aureus propagation in a host is also disclosed herein. The method comprises contacting the specific host tRNA to the S. aureus RNA in the presence of the test compound. The contacting step is typically carried out in vitro in an aqueous solution, with the tRNA, the S. aureus RNA, and the test compound in the aqueous solution. The term "S. aureus RNA" is intended to encompass both a complete S. aureus genome and fragments thereof that contain the tRNA binding portions (such fragments will typically be at least 10 or 12 to 50 or more nucleotides in length). The contacting step may again be carried out with a single test compound or with a library of probes or test compounds in any of a variety of combinatorial chemistry systems, as discussed in greater detail below.

After the contacting step, the next step involves determining whether the compound inhibits the binding of the specific host tRNA to the S. aureus RNA in the presence of the test compound. The determining step can be carried out by any suitable means, such as gel shift assays, chemical and enzymatic footprinting, circular dichroism and NMR spectroscopy, equilibrium dialysis, or in any of the binding detection mechanisms commonly employed with combinatorial libraries of probes or test compounds as discussed below. The inhibition or antagonism of binding indicates that the test compound is useful for inhibiting propagation of the S. aureus in the host. Such compounds are also sometimes referred to as "active compounds" herein. The method may be carried out with S. aureus. In one embodiment the specific host tRNA is mammalian, preferably primate or specifically human, such as $tRNA^{arg}_{SUU}$, and the determining step comprises determining whether the compound inhibits the binding of $tRNA^{arg}_{SUU}$ to the S. aureus RNA.

As noted above, the present invention can be used with test compounds (or "probe molecules"), or libraries (where groups of different probe molecules are employed), of any type. In general, such probe molecules (including those that are active compounds herein) are organic compounds, including oligomers such as antisense olionuleotides, non-oligomers, organo-metallic compounds, and combinations thereof, as well as bio-inorganic compounds. Non-oligomers include a wide variety of organic molecules, such as heterocyclics, aromatics, alicyclics, aliphatics and combinations thereof, comprising steroids, antibiotics, enzyme inhibitors, ligands, hormones, drugs, alkaloids, opioids, benzodiazepenes, terpenes, prophyrins, toxins, and combinations thereof. Oligomers include peptides (that is, oligopeptides) and proteins, oligonucleotides such as DNA, RNA and their derivatives such as peptide nucleic acid (PNA), oligosaccharides, polylipids, polyester, polyamides, polyurethans, polyureas, polyethers, poly(phosphorus derivatives) such as phosphates, phosphonates, phosphoramides, phosphonamides, phosphites, phosphinamides, etc., poly(sulfur derivatives) such as sulfones, sulfonates, sulfites, sulfonamides, sulfenamides, etc., where for the phosphorous and sulfur derivatives the indicated heteroatom for the most part will be bonded to C, H, N, O or S, and combinations thereof. Numerous methods of synthesizing or applying such probe molecules on solid supports (where the probe molecules may be either covalently or non-covalently bound to the solid support) are known, and such probe molecules can be made in accordance with procedures known to those skilled in the art. See, e.g., U.S. Pat. No. 5,565,324 to Still et al., U.S. Pat. No. 5,284,514 to Ellman et al., U.S. Pat. No. 5,445,934 to Fodor et al. (the disclosures of all United States patents cited herein are to be incorporated herein by reference in their entirety); J. Baldwin and I. Henderson, Recent Advances in the Generation of Small-Molecule Combinatorial Libraries: Encoded Split Synthesis and Solid-Phase Synthetic Methodology, Med. Res. Reviews 16, 391-405 (1996).

Such probe molecules or active compounds could be used as inhibitors by contacting the tRNA, the RNA to which the tRNA binds (mRNA, ribosomal RNA) or the modification enzyme responsible for the unique or unusual chemistry or structure of the tRNA (i.e., the modified base).

I. Methods for Identifying an Inhibitor of S. aureus Propagation

Inhibitors of S. aureus propagation can be identified using the methods described herein. The S. aureus propagation can be inhibited, for example, by inhibiting S. aureus translation of RNA to proteins.

The theory behind the methods for identifying inhibitors of S. aureus propagation, and a way to carry out the method, are discussed below.

Identifying Inhibitors of S. aureus Protein Translation

In one aspect, the method can be used to identify inhibitors of S. aureus translation/protein expression. In another aspect, the methods can be used to identify inhibitors of tRNA binding to a target nucleic acid molecule. In another aspect, the methods can be readily adapted for use in high through-put assays. Transfer RNA (tRNA) is involved in translation through the recognition of a corresponding site on the S. aureus genome priming translation. Identifying inhibitors of translation/protein expression may lead to the identification of therapeutic compounds for use in treating S. aureus infection in a host cell and organism.

The method comprises forming a mixture having a tRNA anticodon stem-loop (ASL) fragment, a target nucleic acid molecule that is capable of binding to the tRNA fragment, and a test compound. In one aspect, the target nucleic acid molecule corresponds to a fragment of the S. aureus genome involved in translation, specifically, involved in incorporation of arginine residues, and, more specifically, incorporation of arginine residues using a tRNA specific for S. aureus, into a protein or peptide necessary for the bacteria to survive.

The resulting mixture is incubated under conditions that allow binding of the tRNA fragment and the target nucleic acid in the absence of the test compound. The method further involves detecting whether the test compound inhibits or antagonizes the binding of the tRNA fragment to the target nucleic acid, where the absence or antagonism of binding of the tRNA ASL fragment and the target nucleic acid molecule is indicative of the test compound being an inhibitor of S. aureus propogation.

In one aspect, the detection involves the use of labels to detect the inhibition or antagonism of binding of the tRNA fragment to the target nucleic acid molecule. In one embodiment, the labels are fluorescent labels. However, other detection technologies can also be used for this assay. One alternative, Förster resonance energy transfer (abbreviated FRET), has many variations. FRET is a mechanism describing energy transfer between two chromophores. A donor chromophore, initially in its electronic excited state, may transfer energy to an acceptor chromophore (in proximity, typically less than 10 nm) through nonradiative dipole-dipole coupling. This mechanism is termed "Förster resonance energy transfer." When both chromophores are fluorescent, the term "fluorescence resonance energy transfer" is often used instead, although the energy is not actually transferred by fluorescence. In order to avoid an erroneous interpretation of the phenomenon that (even when occurring between two fluorescent chromophores) is always a nonradiative transfer of energy, the name "Förster resonance energy transfer" is preferred to "fluorescence resonance energy transfer"—the latter enjoys common usage in scientific literature. FRET is analogous to near field communication, in that the radius of interaction is much smaller than the wavelength of light emitted. In the near field region, the excited chromophore emits a virtual photon that is instantly absorbed by a receiving chromophore. These virtual photons are undetectable, since their existence violates the conservation of energy and momentum, and hence FRET is known as a radiationless mechanism. From quantum electrodynamical calculations, it is determined that radiationless (FRET) and radiative energy transfer are the short- and long-range asymptotes of a single unified mechanism.

As used herein, in a FRET assay, one component (acceptor or donor) is attached to the RNA oligomer representing the ASL, and the other (acceptor or donor) to either the ribosome or the mRNA. When the complex is assembled, the FRET components will be close enough for energy transfer. Thus, after incubation in the presence of compounds as described in the protocol, differential signals will be obtained, depending upon how much of the ASL remains bound to the complex.

Protein Synthesis

One pathway ideally suited for novel antibiotic discovery is protein synthesis, which involves the ribosome and several types of enzymes. Both the ribosome and the enzymes bind to specific RNA sequences (FIG. 1). What is lacking for the discovery of new classes of antibiotic compounds that target protein synthesis at the ribosome is a method by which to screen large numbers of compounds that may interfere with these RNA interactions. Ashraf (1999), Phelps (2004) and others have discovered that the ribosome:RNA interactions occur at a much higher frequency and with greater affinity in regions of the RNA that contain modified nucleotide bases.

As shown in FIG. 1, protein synthesis requires the involvement of nonfunctional RNA. The nonfunctional RNA(**) which is a substrate of the modifying enzyme is converted to functional RNA either by modifying one or more nucleotide bases. The anticodon stem loop (ASL) of tRNA(*) that contains modified nucleotide bases interacts with the ribosome to transfer specific amino acids to the on-going protein synthesis process.

Figure 2:
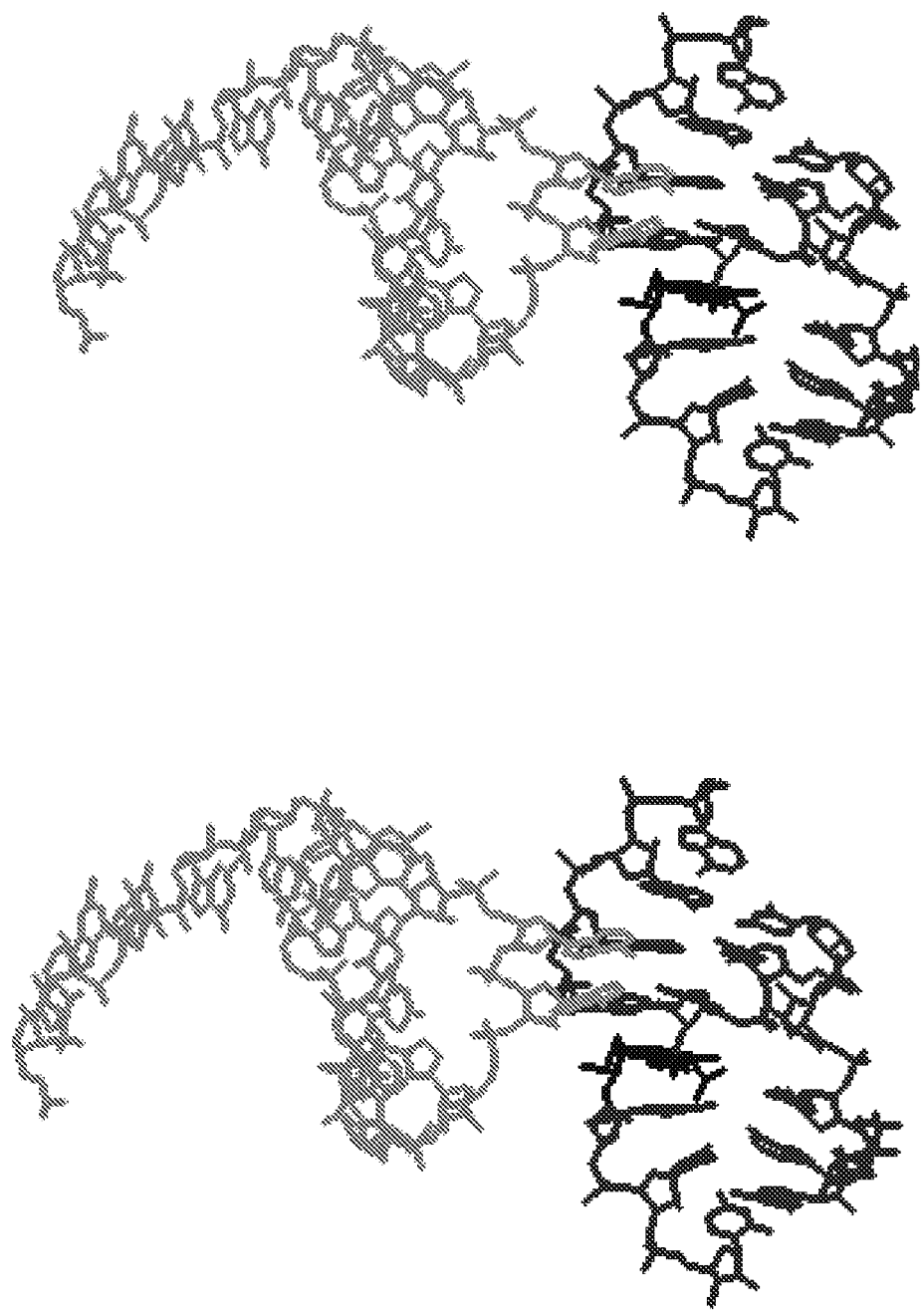
FIG. 2 is a graphic illustration showing "spacefill" and "wire" displays of the structure of tRNA$^{Lys}$ ASL (red) bound to the ribosome (green) at the translocation site. The blue nucleotide embedded in the binding site is the modified nucleotide t$^6$A$_{37}$ on the ASL.

Recent crystallographic investigations illustrate that the post-transcriptional modifications of some tRNAs play an essential role in tRNA recognition by the ribosome translocation site (Phelps et. al. 2004, FIG. 2). These crystallographic studies of the ribosome with ASLs have revealed that the basis for tRNA recognition is a specific group of modified ribosomal residues (FIG. 2).

In addition, binding studies utilizing synthetic RNA oligomers representing the ASL that contains various modified nucleotide bases have also demonstrated an increased affinity of the ribosome with the oligomer containing the modified nucleotide base(s) over the RNA oligomers with unmodified nucleotide bases.

The Role of Modified Nucleotides in Translation

Figure 7:
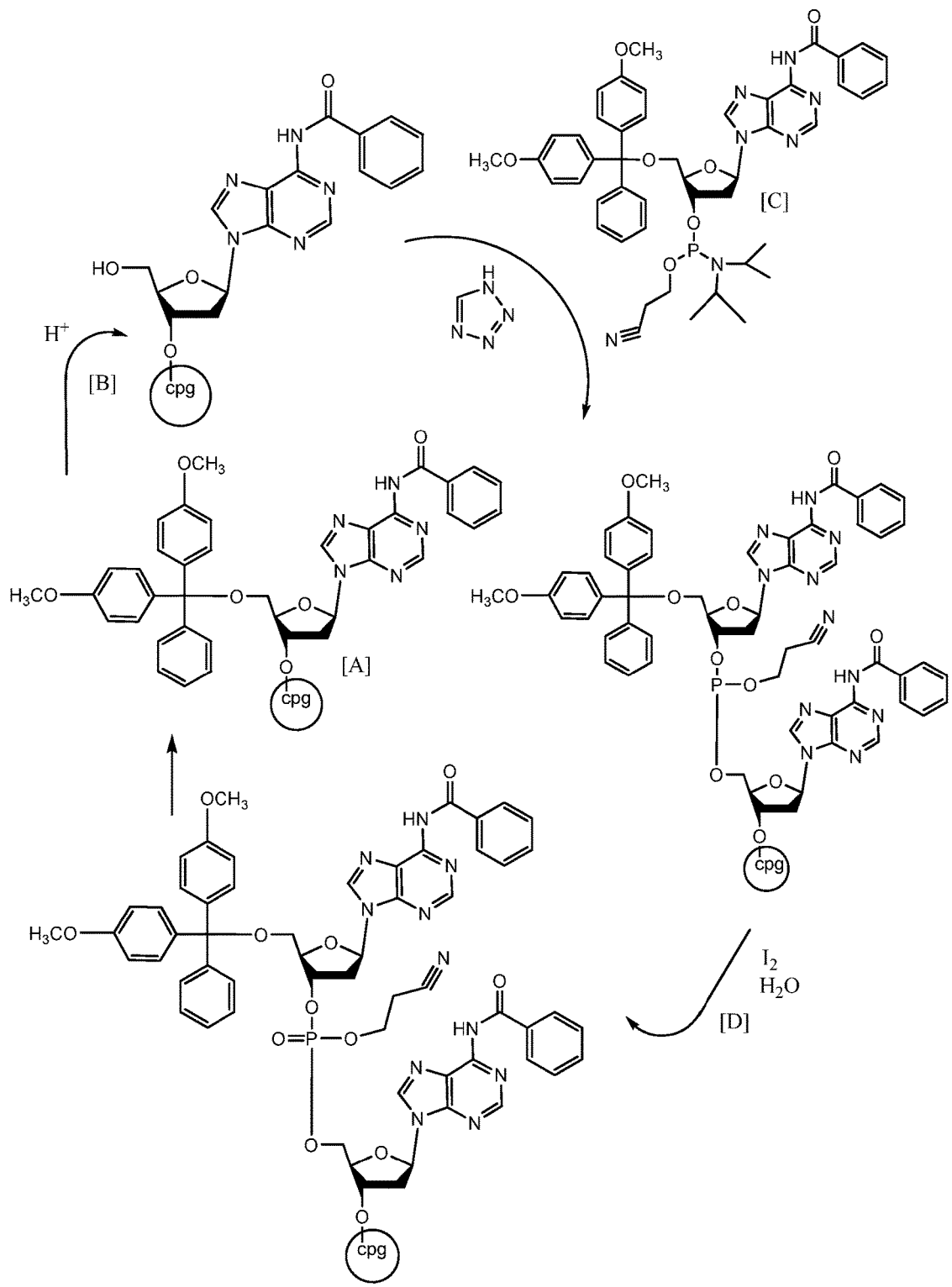
FIG. 7 is a chemical illustration showing the complete synthesis cycle for tRNA synthesis, including de-blocking (A), base condensation (B), capping (C), and oxidation (D) are illustrated. This cycle is completed once for each additional base desired.
Figure 8:
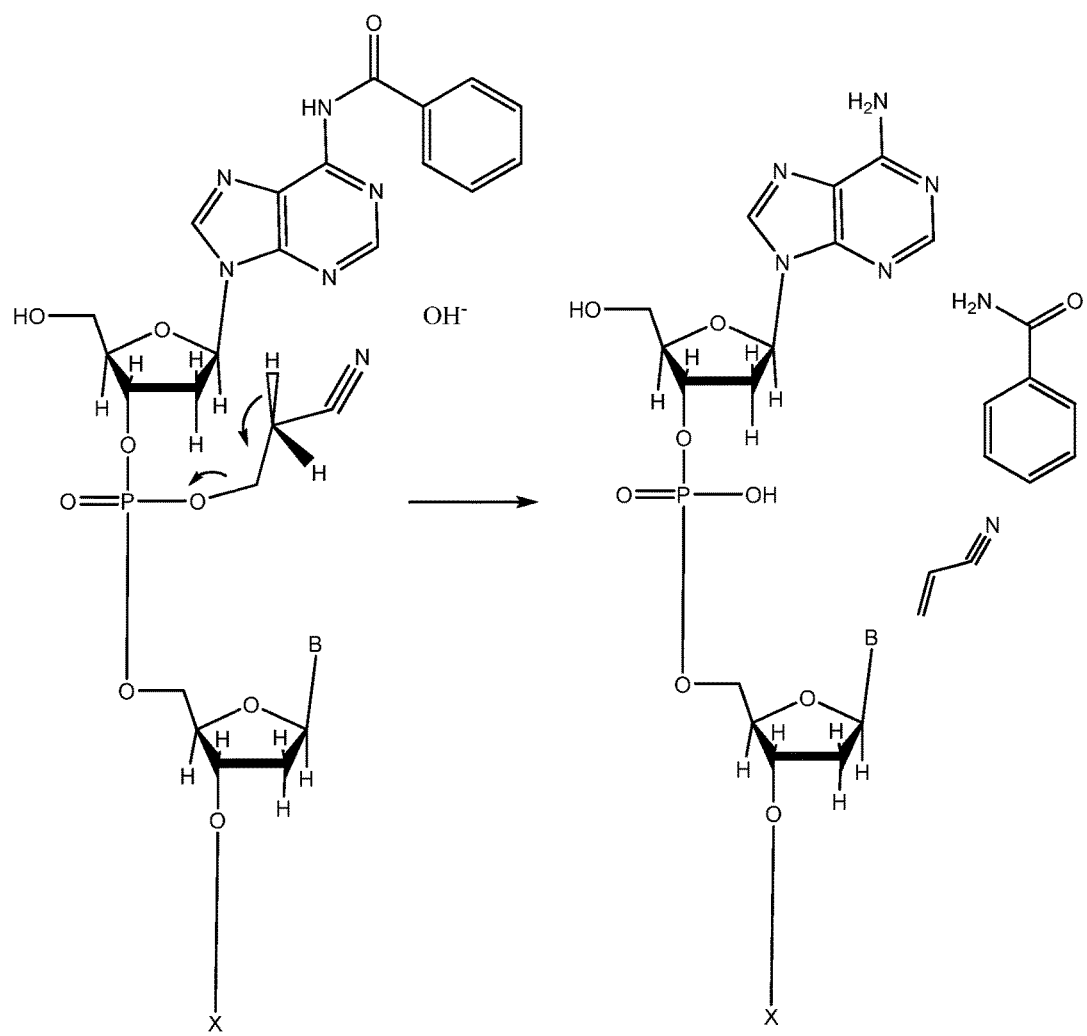
FIG. 8 is a graphic illustration showing the cleavage of a group protecting a heterocyclic primary amine and a cyanoethyl group, using concentrated ammonia, as typically performed in DNA oligonucleotide synthesis.

The academic research in the labs of Dr. Paul Agris, NC State University, and Dr. Andrzej Malkiewicz, of the Technical University of Lodz, Poland has focused on understanding the role of the natural post-transcriptional modifications in RNA structure and function (U.S. Pat. No. 6,461,815), Agris et. al. 2004). These modifications are enzyme catalyzed and can be as simple as the addition of a methyl group or they can be quite complex involving a multi-enzyme process, as shown in FIG. 7.

The details of tRNA' binding and the critical role of tRNA modifications have been determined at the ribosomal translocation site. FIG. 2 is a recently resolved structure of a $tRNA^{Lys}$ ASL bound to the ribosome at the translocation site of Thermus thermophilus (Murphy et. al., 2004). The atomic resolution structure provides evidence that the basis for increased binding of the native modified $tRNA^{Lys}$ ASL compared to an unmodified ASL is specific atomic interactions with the modified base. While the structural details are less understood, modifications to the nucleotide bases in the anticodon stem loop of tRNA significantly increase the affinity of tRNA to the ribosome at both A and P binding sites (Ashraf et. al. 1999).

Figure 3:
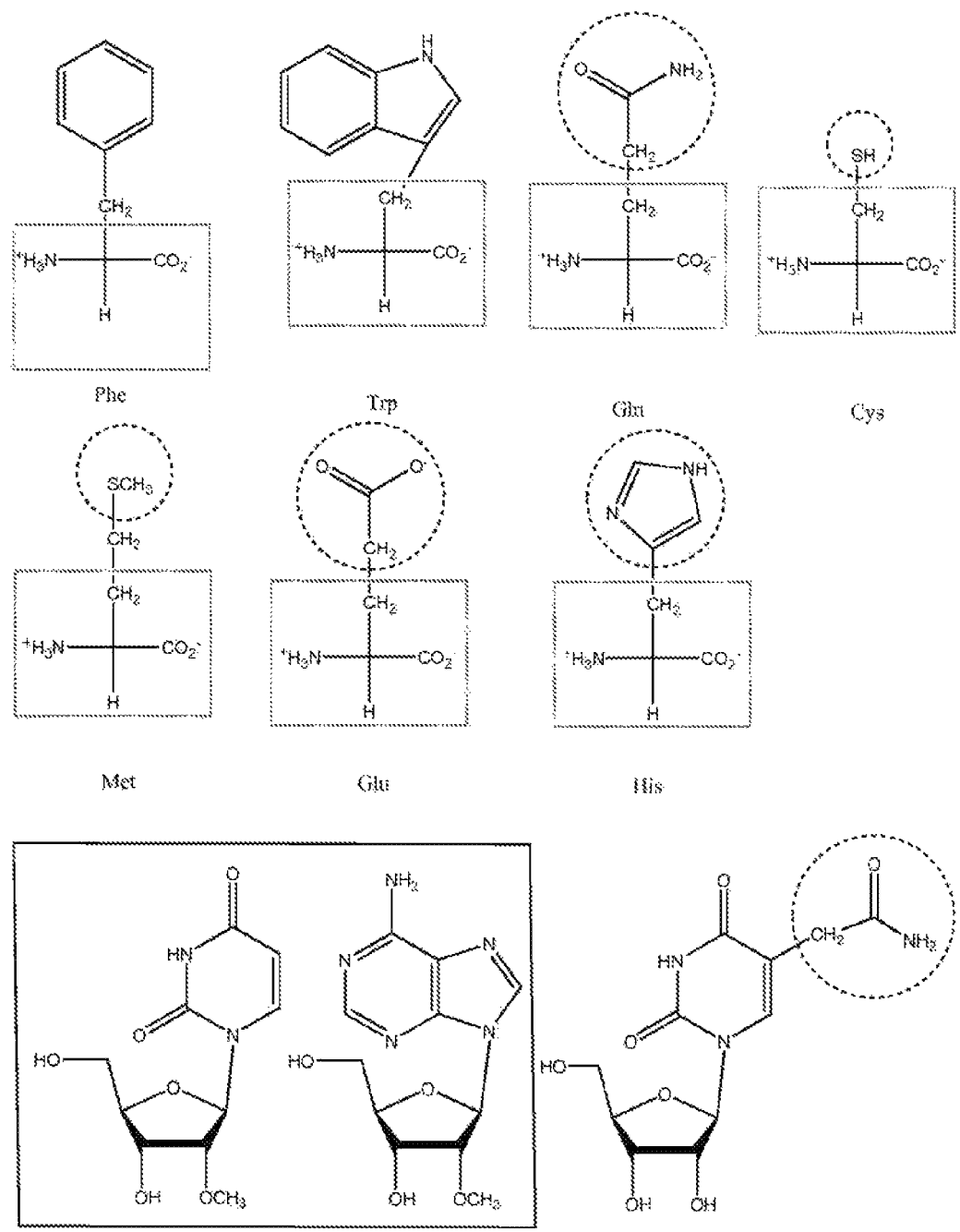
FIG. 3 is a graphic illustration of examples of modified nucleotide bases along bottom row with modifications in circles. Unmodified RNA bases uracil and adenine (in box) are included for comparison. Along the top row are amino acids with functional R-group equivalence to the corresponding nucleotide base in the bottom row.

Over 100 different naturally occurring modified nucleotides are found in all classes of RNA and all kingdoms of organisms (Limbach et. al. 1994). One to two percent of all RNA nucleotides are modified. These nucleotide base modifications are frequently found near catalytic sites of RNAs and many of the proteins that are responsible for the modification are encoded by essential genes (Zhang 2004). In FIG. 3, the modified portions of some example nucleotide bases are circled along with the corresponding site on different amino acids to highlight the area of interaction and increased chemical affinity between the nucleotide base and the amino acid. The researchers in Agris and Malkiewicz labs have taken an approach to study model systems produced by chemical synthesis methods rather than using modified nucleotide bases obtained from biochemical methods (Agris et. al. 1995). This synthetic approach provides far more control to investigate, in detail, the significant contributions made by modified nucleotides. Studies using synthetic nucleotide bases have demonstrated the essential role that RNA modifications have in binding at the ribosome as well as in protein synthesis (Hermann, 2005; Francois, et. al. 2005). This approach has also been used in biophysical studies to determine the thermodynamic contribution of modifications (Agris et. al. 1999). In structural studies, this synthetic approach has been able to demonstrate the role of the modified nucleotide basis in producing new structures which are critical in functional capacities (Agris, et. al. 1997).

Synthesis of Modified Nucleotides and Oligomers:

Synthetic approaches to produce tRNA mimics are known (Agris, et. al. 1995), and involve synthesizing modified nucleotide bases, also known as phosphoramidites (ibid), which are used to synthesize RNA oligomers (Ogilvie et. al. 1988). Synthetic approaches overcome the substantial barrier of obtaining sufficient amounts of natural products for the functional characterization studies. In addition to providing the fully modified ASL for characterization of the tRNA:ribosome binding, the synthetic approach allows for the preparation of intermediate forms of the modified material that can further elucidate the individual contribution of each modification step in enhanced tRNA binding. These mimics have been used to demonstrate that the nucleotide modifications to the anticodon increase the affinity of the tRNA for the ribosome by three orders of magnitude (Ashraf, et. al. 1999; Preliminary Data Section 4).

Using oligomers containing modified nucleotide bases, experiments have been conducted related to some of the key components used in the assays described herein for identifying inhibitors that interfere the binding of the tRNA with the ribosome during translation (FIG. 1), and which have potential as active pharmaceutical agents. In one embodiment, the assays are carried out in a high throughput screening (HTS) assay format.

Characterization of tRNA Binding to the Ribosome In Vitro.

The binding of tRNA to programmed ribosomes can be replicated in vitro (von Ahsen 1997 Ashraf 1999). Schilling-Bartetzko et. al. (1992) discovered that ribosomes could be purified and programmed with a message and that tRNA would bind to various sites on the ribosome based on the solution conditions. These binding reactions are currently performed as individual reactions with the ASL:ribosome complex being bound to filter papers. In addition to these reactions being conducted in a large volume, they use radioactive materials for detection and quantitation. While these methods do provide an approach to characterize tRNA:ribosome binding, they are not compatible with HTS assays due to the size of the reaction vessel, the radioactive detection methodology, and the subsequent radioactive waste disposal. A fluorescent method of detection to monitor tRNA binding to the ribosome has been developed (Wells et. al. 1980) that can be adapted to an HTS format.

Preliminary Data:

The screening methods described herein use translation as a biochemical target, where the ASL of tRNA containing modified nucleotides is essential to translation, the modified bases and RNA ologimers containing these modified bases can be synthesized using the techniques described herein, and these oligomers bind to programmed ribosomes. A series of experiments was conducted to demonstrate that a fluorescently-labeled synthetic oligomer containing 17 nucleotide bases, 3 of which are modified, (FIG. 4) will bind to programmed ribosomes isolated from S. aureus, and that this binding can be detected by monitoring the change in fluorescence.

Figure 5:
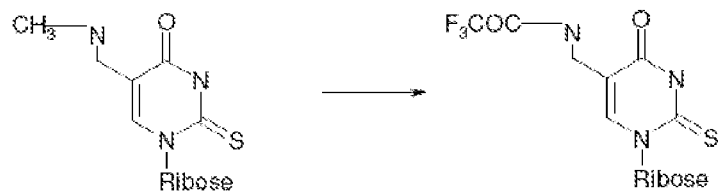
FIG. 5 is a chemical drawing showing the protection of the modified nucleotide bases prior to synthesis of the RNA oligomer. Panel A illustrates protection with trifluoryl acetic acid. Panel B illustrates protection with benzoyl. Panel C outlines the major steps in the conversion of adenosine to t6A. And, panel D illustrates the general protection scheme of the ribose hydroxyl groups.
Figure 5:
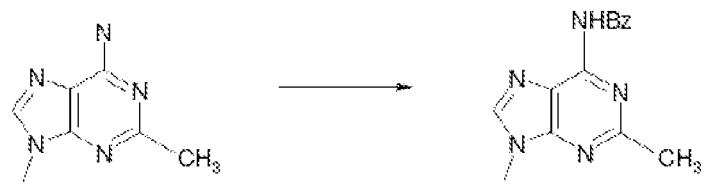
Figure 5:
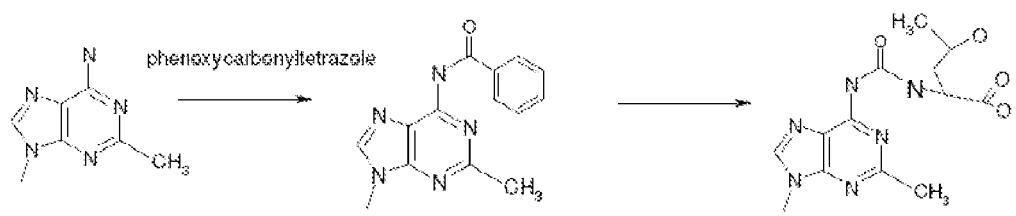
Figure 5:
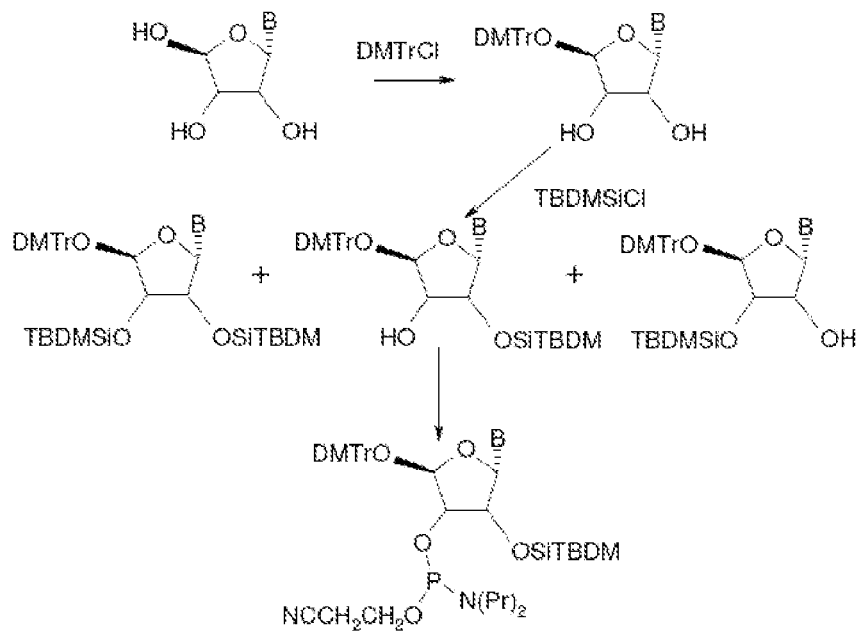
Figure 6:
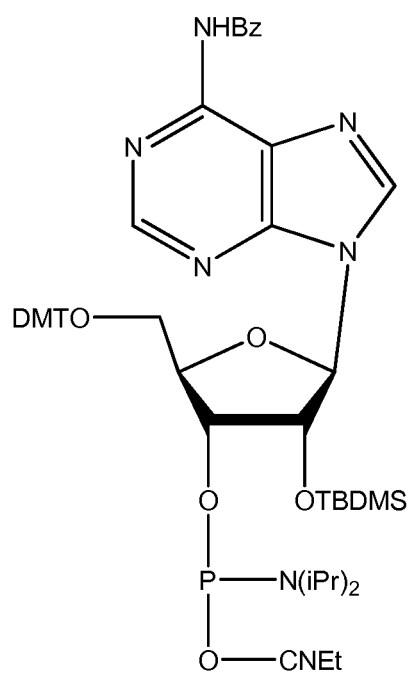
FIG. 6 is a chemical illustration of a Bz-A-CE RNA phosphoramidite monomer showing the Bz ("benzyl") protecting group on the base and the Silyl sugar protecting group TBDMS ("t-butyldimethylsilane").

In moving from a manual radioactive filter based assay to a format suitable for adaptation to a HTS format, efforts were focused in two objectives. Concurrent efforts were made on the preparation of the phosphoramidite components for the synthesis of a modified oligonucleotide (FIG. 5) while experiments were performed to adapt the assay format.

To perform the HTS assay described, the substrates (oligomers which contain modified nucleotides) must be prepared, detection methodologies developed, and standard methods converted to high throughput methods. The RNA oligomers described herein serve as a ribosome substrate in an HTS assay, and, as discussed below, data was obtained to support the selection of the RNA oligomer to use as a substrate, and the assay format (filter paper vs. in solution).

Selection of Test Sequence.

The initial survey of the modification requirement for an ASL to bind to the ribosome (Yarian 2002) identified several different ASL where the unmodified oligomer poorly bound to programmed ribosomes. These ASLs become good candidates for tools to be used to screen for compounds that can block selected tRNA from binding to the ribosome and selectively inhibit bacterial protein synthesis. Based on the phosphoramidites available for oligonucleotide synthesis tRNA$^{Arg}_{UCU}$ was selected. Using the complete genome for S. aureus the sequences of tRNA$^{Arg}_{UCU}$ were surveyed and a single sequence was found for the multiple copies in the genome, as shown in FIG. 4. FIG. 4 is an illustration of a synthetic oligomer representing the anticodon stem loop from tRNA$^{Arg}$ in S. aureus. When the modifications are present, the ASL binds to programmed ribosomes isolated from S. aureus, which binding can be detected by monitoring the change in fluorescence. The synthesis of the AS$^{Ar}$-$g_{UCU}$ has been completed, and the correctness of the composition was confirmed by mass spectrometry analysis.

Synthesis of Modified Nucleotide Base(s) and RNA Oligomers:

The modified nucleotides found in the tRNA$^{Arg}$ ASL from S. aureus (Agris et. al. 1995, Ashraff, 1999, unpublished data 2007) can be prepared as described herein. As previously shown in FIG. 4, the tRNA$^{Arg}$ ASL contains 1 modified base denoted as t6A (Ryszard et. al. and Sundaram, et. al.), and 2 modified nucleotides, s2C and mnm5U.

In general, functional groups on the modified nucleotide bases are protected using phosphoramidite chemistry (Ogilvie et. al. 1988). Using this chemistry, different modified nucleotides can be incorporated into a range of oligonucleotides ranging in length from 3 to 36 nucleotides (Nobles et. al. 2002). The protecting groups are subsequently removed after synthesis of the RNA oligomer. The addition of a protecting group to each modified base and ribose is described below. Because the 2 position thio-groups in the modified RNA nucleotides can be oxidized in standard RNA synthesis, an alternative oxidizing agent, tert-butyl hydroperoxide (10% solution in acetonitrile) (Kumar and Davis, 1997), can be used during synthesis of the oligomer. Synthetic RNA oligomers prepared according to these methods have been used in both functional (Yarian 2000, 2002 and Phelps 2004) and structural studies (Stuart 2000 and Murphy 2004).

Modified Nucleotide t6A Phosphoramidite

Preparation of the N6-(N-threonylcarbonyl) adenosine for automated synthesis followed a slightly different approach than that for the other phosphoramidites (Panels A, B, and C). The first step was to protect the ribose functions of adenosine. Next, the ribose protected adenosine was reacted with 3 equivalents of phenoxycarbonyltetrazole in anhydrous dioxane for 18 hr at 37° C. to produce phenyl carbamates at the six position. This was followed by aminolysis with 3 equivalents of crystalline L-threonine p-nitrobenzyl ester in anhydrous dioxane, for 18 hr at 37° C., producing the N6-(N-threonylcarbonyl) adenosine. The t6A carboxylate was then protected by a trimethylsilylethyl group, in a manner similar to that used to protect the ribose function. Finally the phosphoramidite was phosphitylated following the protocol described above.

Modified Nucleotides s2C and mnm5U

These modified nucleotides were synthesized as follows. In general, the exo-amino function of the core nucleotide base, C or U, was protected following a scheme similar to Malkiewicz (Malkiewicz et. al. 1983). Following protection of the nucleotide base, the ribose function was then protected and phosphitylated using these general procedures (Panel C). The protected nucleotide was dried by co-evaporation twice with pyridine and dissolved in pyridine. Tert-butyldimethylchlorosilane and imidazole were added and reacted for 4 hours at room temperature. The excess silyl chloride was decomposed with water and dichloromethane. The aqueous layer was extracted twice with dichloromethane and combined with the organic layer. The solvent was evaporated by vacuum yielding a gum which was dissolved in ether and precipitated by pouring slowly into petroleum ether (40-60° C.) with stirring. The precipitate was collected and washed twice with petroleum ether. At this point the crude product contained three components; the 2',3' disilylated, 2' silylated (major product) and 3' silylated. The pure 2' protected isomer was obtained by silica gel column chromatography. This product was then ready for phosphitylation.

The N-protected-5'-O-dimethoxytrityl-2'-O-tertbutyldimethylsilyl-ribonucleotides were dried by two co-evaporations with anhydrous pyridine and THF. The residue was dissolved in anhydrous THF under argon. Dimethylaminopyridine, N,N,N-ethyidiisopropylamine and cyano-ethoxy-diisopropy amino-chlorophosphine were added through a rubber septum. After 2 hours the reaction mixture, was quenched with ethyl acetate and washed with 5% sodium bicarbonate followed by water. Aqueous washes were back extracted with ethyl acetate. Combined organic layers were dried over sodium sulphate and the solvent was evaporated yielding viscous oil. The product was co-evaporated twice with toluene and the pale yellow phosphoramidite products were purified by flash silica gel chromatography.

Synthesis of RNA Oligomers Containing Modified Nucleotide Bases:

The RNA oligomer was synthesized and purified following protocols developed specifically for these modified reagents (Agris et. al. 1995, Murphy et. al. 2004). Purification of the oligomers was by HPLC as previously described (Agris et. al., 1999). Purity of the oligomer was confirmed by gel electrophoresis and proper incorporation of the modified nucleotide bases was confirmed by mass spectrometry.

In addition to the $ASL^{Arg}$ containing the 3 modified nucleotide bases, $ASL^{Arg}$ containing no modified bases and a random 17mer oligomer were synthesized to be used to demonstrate specificity and as a negative control, respectively. All oligomers were tagged with fluorescein on the 3' end.

In general, the synthesis of an RNA oligomer requires that all of the major functional groups on each nucleotide base be protected during the formation of the oligomer and then deprotected after synthesis. The general protection, deprotection and oligomer synthesis schemes developed by the company founders are described in the following paragraphs.

Procedures for Deprotecting Synthetic Oligoribonucleotides (RNA Oligos)

Several protecting groups are available and can be selected based upon the specific chemistry of each nucleotide base (FIG. 5); thus, the protection group on the RNA phosphoramidite monomers to a large extent will dictate the strategy for deprotection. It is routine in the art to remove silyl protecting groups with tetrabutylammonium fluoride solution and triethyamine trihydrifluoride.

For regular deprotection of the phosphoramidite protecting groups, ethanolic ammonium hydroxide can be added to the vial containing the beads from the synthesis process and incubated—time specific to the types of protecting groups. Tetrabutylammonium fluoride can be added to the residue from the deprotection step to remove silyl protecting groups on the sugars. The 4 steps described in the following paragraphs can be used to add each nucleotide to the oligomer, as illustrated in FIG. 7.

Step A: De-Blocking

The first base, which is attached to the solid support, is at first inactive because all the active sites have been blocked or protected. To add the next base, the DMT group protecting the 5'-hydroxyl group is removed. This is done by adding an acid, such as dichloroacetic acid (DCA) or trichloroacetic acid in dichloromethane (DCM), to the reaction column. The 5'-hydroxyl group is now the only reactive group on the base monomer. This ensures that the addition of the next base will only bind to that site. The reaction column is then typically washed to remove any extra acid and by-products.

Step B: Base Condensation

The next base monomer cannot be added until it has been activated. This can be achieved by adding tetrazole to the base. Tetrazole cleaves off one of the groups protecting the phosphorus linkage. This base is then added to the reaction column. The active 5'-hydroxyl group of the preceding base and the newly activated phosphorus bind to loosely join the two bases together. This forms an unstable phosphite linkage. The reaction column is then washed to remove any extra tetrazole, unbound base and by-products.

Step C: Capping

When the activated base is added to the reaction column, some does not bind to the active 5'-hydroxyl site of the previous base. If this group is left unreacted, it is possible for it to react in later additions of different bases. This would result in an oligonucleotide with a deletion—and an incorrect sequence manufactured. To prevent this from occurring, the unbound, active 5'-hydroxyl group is capped with a protective group which subsequently prohibits that strand from growing again. The "cap" is typically an acetyl group, which is formed by adding acetic anhydride and N-methylimidazole to the reaction column, where the acetic anhydride reacts with the 5'-hydroxyl group.

Step D: Oxidation

In step 2, the next desired base can be added to the previous base, resulting in an unstable phosphite linkage. To stabilize this linkage, a solution of dilute iodine in water, pyridine, and tetrahydrofuran (when synthesizing DNA) can be added to the reaction column. For RNA syntheses, see previous paragraphs describing techniques for consideration made at this step. The unstable phosphite linkage can be oxidized to form a much more stable phosphate linkage.

These steps can be repeated until all desired bases have been added to the oligonucleotide. After all bases have been added, the oligonucleotide is cleaved from the solid support and deprotected.

S. aureus Ribosome Assay Development:

The assay development experiments initially used unmodified 17 nucleotide control ASLs complementary to E. coli tRNA$^{Phe}$, which are able to bind to ribosomes programmed with a poly U message. The initial control sequences tested both a 3' and 5' fluorescein to determine if location of the fluorophore affected the limit of detection or affinity of the ASL to the ribosome. Titrations of the fluorescent ASL under a range of conditions were made to determine that the limit of detection was about $3 \times 10^{-7}$M, which is suitable for the needs of the assay.

This preliminary data was used to determine starting conditions to test if a filter disk protocol could be modified to a 96 well plate assay, such as a 96 well filtration plate assay, using a Millipore 96 well HTS filter plate. By slightly modifying the conditions used in the filter assay, message dependent ASL binding was observed, and a comparable tRNA ribosome binding activity obtained for the whole tRNA in a radiochemical activity. Using buffer conditions similar to the initial binding steps in the filter assay, addition of the ASL to the programmed ribosome resulted in a quenching of the ASL fluorescence in a specific manner. These results indicate that the oligomer is binding to the programmed ribosome and that this binding is detectable by monitoring the change in fluorescence.

During translation, ribosomes are programmed to accept tRNA carrying the appropriate amino acid. For this project, ribosomes are programmed to receive the tRNA associated with ASL$^{Arg}$ using the message, poly AGA. The binding affinity of correctly modified ASL to ribosomes programmed with short messages is comparable to those observed for native tRNA and full message (Ashraf et. al. 1999); thus, confirming that the entire tRNA is not required for effective ribosomal binding.

Thus, a series of experiments were conducted: i) to demonstrate that the synthetic RNA oligomer containing the 3 modified nucleotide bases described above binds to programmed ribosomes using the historical filter paper technique and that this binding could be monitored using fluorescent detection in a 96-well plate format; ii) to demonstrate specificity of the programmed ribosomes to the ASL$^{Arg}$; iii) to demonstrate that this filter based assay could be converted to an HST compatible solution based assay by monitoring the differential fluorescent signal associated with bound vs. unbound ASL$^{Arg}$; and, iv) to determine that an acceptable limit of detection could be achieved with the solution based assay.

Figure 9:
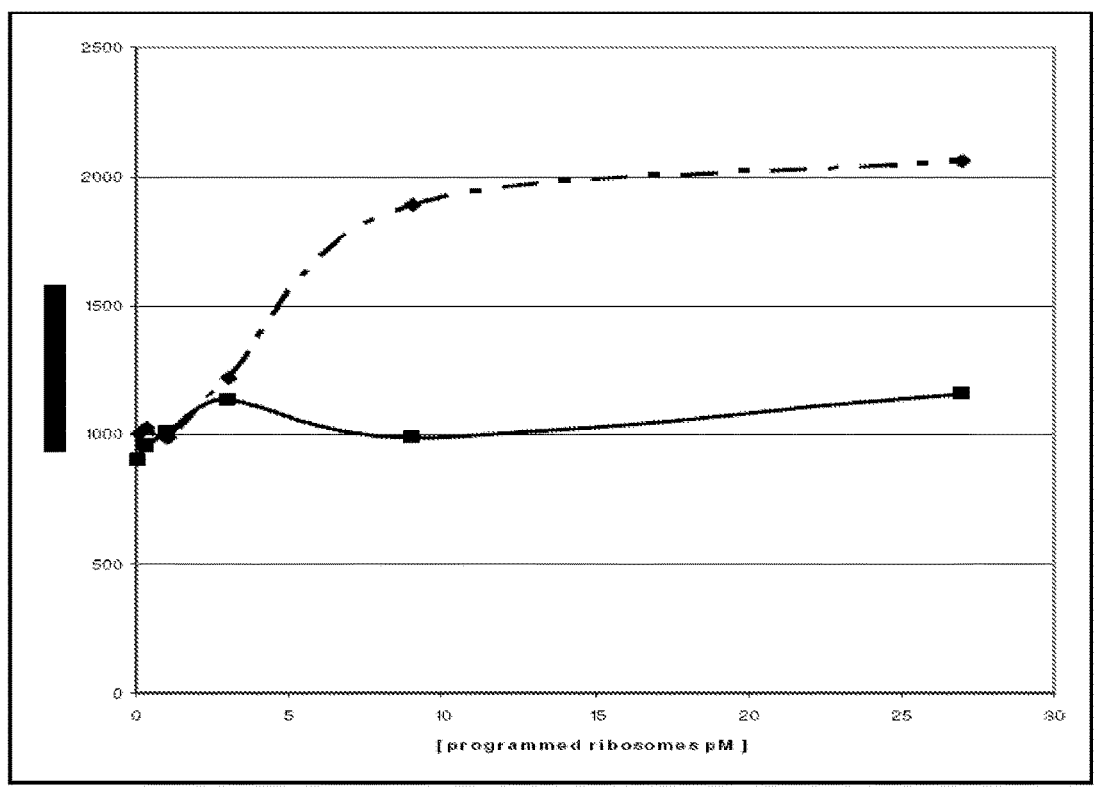
FIG. 9 is a chart showing the titration of fluorescently labeled ASL with programmed ribosomes (dashed line) and unprogrammed ribosomes (solid line).

The limit of detection was determined, and it was confirmed that only minimal non-specific retention of ASL by the filter manifold occurred. Titrations of the fluorescent ASL under a range of conditions were made to determine that the limit of detection was about $3 \times 10^{-7}$M, establishing an acceptable working concentration range for the fluorescently-labeled ASL. These data were used to determine starting conditions for the assay. Using a 96-well filtration plate assembly in conjunction with a Millipore 96 well HTS filter plate, message dependent ASL binding was observed (FIG. 9), i.e. binding of the fluorescently labeled RNA oligomer increased significantly in programmed vs. unprogrammed ribosomes. These results are comparable to tRNA ribosome binding activity obtained for the whole tRNA in a radiochemical activity assay.

The assay described herein can detect binding of the RNA oligomer to programmed ribosomes specific to the ASL$^{Arg}$ oligomer.

Use of Combinatorial Chemistry to Identify and Optimize Leads

The assay can be used to identify active compounds that are specific to S. aureus. Mechanistically and biologically active hits can be identified using compound libraries, such as lead generation libraries, i.e., libraries including between around 10 and around 500,000 compounds. In one embodiment, a diverse library is used. In another embodiment, a series of two or more libraries are used. Leads identified in the screening assay can optionally be subjected to mammalian cell toxicity testing, and/or computational modeling.

The assay can be run automatically or manually. The manual assay can be conducted, for example, in 96-well plate format. The conversion of this assay to HTS format typically involves reducing the volumes of the kit components for use in a 384 or possibly 1,536 plate format, and optimizing the conditions for the capabilities available with a given robotic system.

When the volume of all substrates is reduced, the amount of the fluorescent label is also reduced; thus, reducing the amplitude of the signal to be detected. This is generally overcome by using detectors specifically developed for HTS assays or using other means to increase the signal differential between bound vs. unbound substrate. To ascertain the effect of the assay reagents and/or assay conditions on assay performance, each condition can be varied within predetermined ranges and the assay results can be analyzed as described below. Assay conditions can be modified, for example, until a Z-factor between 0.4 and 1 is obtained. Z-factors are an industry standard method for determining when an assay has been optimized.

The HTS assay can be validated, for example, by analyzing a suitable library, with positive and negative controls and/or general toxins that inhibit most assays.

An industry standard diverse chemical library (eg., Preswick library) supplemented in random order with positive and negative controls along with other selected chemicals can be used in this validation experiment. During the first run, this validation will demonstrate that the positive and negative controls can be determined in a consistent manner and that a range of activity is detected in the remaining compounds. This will demonstrate that the assay is robust and functioning properly on the complete robotic system.

Figure 10:
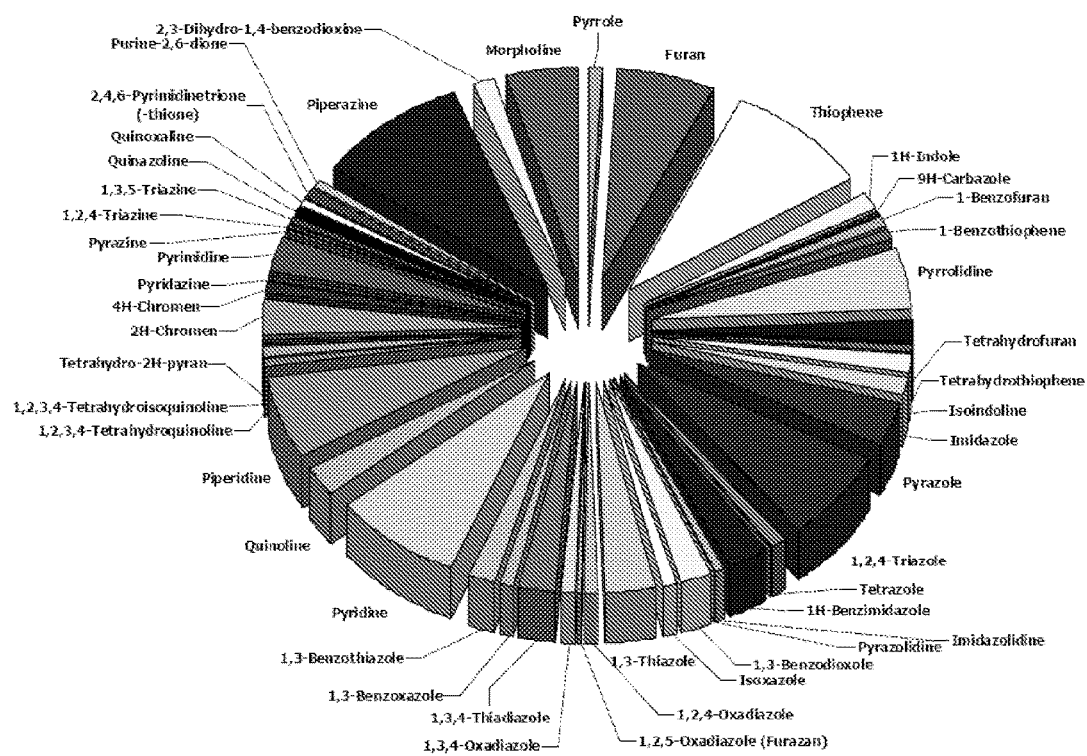
FIG. 10 is a chart showing the chemical diversity of a representative 100k compound library.

A diverse chemical library can be screened using the (ideally validated) assay. As used herein, the term library refers to 100 or more compounds, ideally, 10,000 or more compounds, and preferably, includes a minimum of 100,000 compounds or more. A subset of a diverse chemical library will be screened with the validated assay at a single concentration. Ideally, diverse and targeted libraries will total approximately 500,000 compounds, consisting of a mix of structurally diverse singletons and compound clusters. The clusters are ideally built around a variety of scaffolds, each class containing enough members to provide a preliminary SAR analysis if the entire cluster is screened. The libraries ideally include a modest selection of natural products and known drugs, though natural products were not emphasized during compound acquisition because of their frequent synthetic intractability. The anticipated distribution of one 100k subset, which is a representative compound library, is depicted in FIG. 10.

Depending upon the throughput of the validated assay (384 vs. 1,536 plate format), this typically takes one or two days on a robotic system, and approximately one week for data analysis. Those compounds that demonstrate sufficient inhibitory activity in the assay can be re-screened in a dilution series (5 to 10 concentrations) to confirm that the compounds are inhibitory and to establish $IC_{50}$ and $IC_{90}$ concentrations. A range of inhibitory activity is typically observed in these experiments. Generally, those compounds referred to as 'hits' that demonstrate the strongest inhibitory effects (lower inhibitory concentrations) are selected for advancement to the next step, for example, subsequent screening in biological assays as described herein.

Confirming the Biological Activity of Hits from the HTS

The biological activity of the identified 'hits' from the screening assays described above can be determined by analyzing these hits in a minimum inhibitory compound bacterial screen.

Screening of the 'hits' for antimicrobial activity to determine 1) a single breakpoint concentration of activity against a common Gram-positive and a Gram-negative human pathogen; and 2) whether a "clinically significant" potency can be detected using a threshold concentration, i.e. 32 µg/ml. For determining the single breakpoint of activity, a well-characterized strain of *Escherichia coli* and several strains of *Staphylococcus aureus* with varying types of antibiotic resistance can be tested against each sample. As a minimum inhibitory concentration (MIC), an achievable potency of less than or equal to 32 µg/ml would be considered an active sample worthy of extended study.

Those compounds that are determined to be active at a single concentration can then be tested in a dilution series against the same organisms. Those compounds that are the most active can be advance to the secondary screen described in the next paragraph. The conduct of these first two screens on a limited number of species will allow for a greater number of compounds active at the molecular level to be tested at the whole organism level increasing the opportunity to identify biologically active compounds in a very cost effective manner.

A secondary screen of "active" samples can include an extended dilution screen (for example, eight to 12 $\log_2$ dilution steps) to determine "on-scale" value for a potential antimicrobial agent including evaluation of breadth of spectrum to such organisms, such as staphylococci, streptococci, Enterobacteriaceae, non-fermentative Gram-negative bacilli, anaerobes and yeast species. These isolates are likely recent clinical strains representing wild-type and strains with resistance phenotypes. Methods utilized will be those described above with the addition of NCCLS M11-A6 (anaerobes) and M7-A2 (yeast) or equivalent. Testing against this broader spectrum of organisms can characterize the spectrum of antimicrobial activity. In one embodiment, the compounds will be effective against *S. aureus*, but not against other bacterial species.

Estimating the Mammalian Toxicity of Biologically Active Compounds

The potential mammalian toxicity of biologically active compounds identified in SA assay can be estimated using 3 mammalian cell lines. Compounds that are highly toxic in these assays will be considered to be general toxins with a high probability of interacting with multiple molecular targets. Cytotoxicity assays may be conducted with rat hepatoma H4IIE cell line, rat kidney NRK cell line, and primary human hepatocytes or other mammalian cells. Each cell line can be exposed to 5 concentrations of each test article or with appropriate positive and negative control substances. Three biochemical endpoints will be monitored to determine viability, mitochondrial function, and membrane integrity.

The assay described herein can be used to screen large compound libraries to discover novel antibiotics. The lead compounds identified during the automated HTS can be further developed for the treatment of *S. aureus* infections. The new antibiotics can reduce the potential for developing drug resistance, and can treat currently-existing multi-drug resistant organisms.

A high-throughput screen was performed, as described in the working examples, and the following compounds were identified:

2-[2-(4-Dimethylamino-phenyl)-vinyl]-3-(4-methoxy-phenyl)-3H-quinazolin-4-one

3-Methyl-1-methylamino-3H-naphtho[1,2,3-de]quinoline-2,7-dione

3-Methyl-1-piperidin-1-yl-3H-naphtho[1,2,3-de]quinoline-2,7-dione

2-[2-(4-Dimethylamino-phenyl)-vinyl]-3-o-tolyl-3H-quinazolin-4-one

2-[2-(4-Dimethylamino-phenyl)-vinyl]-3-(4-methoxy-phenyl)-3H-quinazolin-4-one 3-(4-Diethylamino-phenyl)-1-(4-vinyl-phenyl)-propenone 3-(3-Hydroxy-phenylamino)-1-phenyl-propenone 3-Hydroxy-5-phenyl-1-[1,3,4]thiadiazol-2-yl-4-(thiophene-2-carbonyl)-1,5-dihydro-pyrrol-2-one 3-Hydroxy-1-(5-isopropyl-[1,3,4]thiadiazol-2-yl)-5-pyridin-3-yl-4-(thiophene-2-carbonyl)-1,5-dihydro-pyrrol-2-one 2-Allyl-6-morpholin-4-yl-benzo[de]isoquinoline-1,3-dione 6-Azepan-1-yl-2-(3,5-dimethyl-1H-pyrazol-4-yl)-benzo[de]isoquinoline-1,3-dione 6-Piperazin-1-yl-2-o-tolyl-benzo[de]isoquinoline-1,3-dione 2-(4-Methoxy-phenyl)-6-piperazin-1-yl-benzo[de]isoquinoline-1,3-dione N-[4-(6-Hydroxy-1,3-dioxo-decahydro-benzo[de]isoquinolin-2-yl)-cyclohexyl]-acetamide 3-Benzooxazol-2-yl-7-diethylamino-chromen-2-one 3-Benzothiazol-2-yl-8-(2-ethyl-piperidin-1-ylmethyl)-7-hydroxy-chromen-2-one (8-Methoxy-4-methyl-6-oxo-6H-benzo[c]chromen-3-yloxy)-phenyl-acetic acid 7-Diethylamino-3-(5-pyridin-3-yl-[1,3,4]oxadiazol-2-yl)-chromen-2-one 2-(2,4-Dihydroxy-benzoyl)-benzoic acid

[3-Chloro-5-(3,4-dimethoxy-phenyl)-7-trifluoromethyl-pyrazolo[1,5-a]pyrimidin-2-yl]-(4-methyl-piperazin-1-yl)-methanone 1,3-Dimethyl-5-[5-(4-methyl-piperazin-1-yl)-furan-2-ylmethylene]-pyrimidine-2,4,6-trione 5-(4-Bromo-5-morpholin-4-yl-furan-2-ylmethylene)-pyrimidine-2,4,6-trione 5-(5-Morpholin-4-yl-furan-2-ylmethylene)-pyrimidine-2,4,6-trione 5-(5-Morpholin-4-yl-furan-2-ylmethylene)-pyrimidine-2,4,6-trione (4,4,6-Trimethyl-4,5-dihydro-pyrimidin-2-yl)-(4,6,7-trimethyl-quinazolin-2-yl)-amine 4-(4-Methyl-piperazin-1-yl)-2-styryl-quinazoline 2-(4-Bromo-phenyl)-4-piperazin-1-yl-quinazoline N-(2-tert-Butylamino-acenaphthen-1-yl)-benzenesulfonamide 2,2'-[3,6-acridinediylbis(nitrilomethylylidene)]diphenol 8-Amino-1,3-dimethyl-1H-benzo[g]pteridine-2,4-dione 2-Cyclohexylaminomethylene-2H-3a-aza-cyclopenta[a]indene-3,8-dione 3-Bromo-1-[(2-hydroxy-phenylimino)-methyl]-6,7,8,9-tetrahydro-dibenzofuran-2-ol 2-[4-(Acetyl-phenyl-amino)-buta-1,3-dienyl]-3-ethyl-benzothiazol-3-ium N-[5-(4-Chloro-phenyl)-7-phenyl-4,7-dihydro-[1,2,4]triazolo[1,5-a]pyrimidin-2-yl]-methanesulfonamide 2-Ethyl-1-thioxo-1,2,3a,4,9,10-hexahydro-2,9,10a-triazacyclopenta[b]fluoren-3-one 2-[4-(2-Hydroxy-ethyl)-piperazin-1-yl]-N-[4-(6-methyl-benzothiazol-2-yl)-phenyl]-acetamide 7-(4-Chloro-phenyl)-5-thiophen-2-yl-4,7-dihydro-tetrazolo[1,5-a]pyrimidine

[3-(1,3-Dioxo-indan-2-ylidenemethyl)-indol-1-yl]-acetic acid methyl ester 2-(4-Dimethylamino-benzylidene)-7-methyl-3-oxo-5-thiophen-2-yl-2,3-dihydro-5H-thiazolo[3,2-a]pyrimidine-6-carboxylic acid methyl ester

[5-(1H-Indol-3-ylmethylene)-4-oxo-2-thioxo-thiazolidin-3-yl]-phenyl-acetic acid 2-(2,4-Dihydroxy-benzoyl)-benzoic acid (4,4,6-Trimethyl-4,5-dihydro-pyrimidin-2-yl)-(4,6,7-trimethyl-quinazolin-2-yl)-amine.

The compounds useful in the methods described herein have the following formulas.

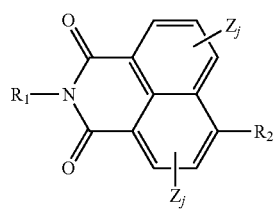

Formula 1 wherein:

$R_1$ is defined as H, $C_{1-6}$ alkyl, $C_{3-10}$ cycloalkyl, $C_{2-6}$ alkenyl, including allyl, aryl, heteroaryl, specifically including pyrazole, thiophene, furan, pyrrole, and imidazole, heterocyclyl, where heterocyclyl specifically includes $C_{5-7}$ azacyclic rings, such as azepane, $C_{5-7}$ azacyclic rings that further include an oxygen atom, such as morpholine, and $C_{5-7}$ azacyclic rings that include two ring nitrogen atoms, such as piperazine, $R_2$ is defined as H, $OR_1$, $SR_1$, $NHR_1$, $C_{1-6}$ alkyl, $C_{3-10}$ cycloalkyl, $C_{2-6}$ alkenyl, including allyl, aryl, heteroaryl, specifically including pyrazole, thiophene, furan, pyrrole, and imidazole, heterocyclyl, where heterocyclyl specifically includes $C_{5-7}$ azacyclic rings, such as azepane, $C_{5-7}$ azacyclic rings that further include an oxygen atom, such as morpholine, and $C_{5-7}$ azacyclic rings that include two ring nitrogen atoms, such as piperazine, Z is defined as defined as $C_{1-6}$ alkyl (including cycloalkyl), alkenyl, heterocyclyl, aryl, heteroaryl, halo (e.g., F, Cl, Br, or I), —OR', —NR'R", —CF$_3$, —CN, —NO$_2$, —C$_2$R', —SR', —N$_3$, —C(C=O)NR'R", —NR'C(=O) R", —C(C=O)R', —C(C=O)OR', —OC(=O)R', —OC(=O)NR'R", —NR'C(=O)OR", —SO$_2$R', —SO$_2$NR'R", and —NR'SO$_2$R", where R' and R" are individually hydrogen, $C_{1-6}$ alkyl, cycloalkyl, heterocyclyl, aryl, or arylalkyl (such as benzyl), wherein alkyl, alkenyl, aryl, heteroaryl, and heterocyclyl moeities can optionally be substituted with a $C_{1-6}$ alkyl (including cycloalkyl), alkenyl, heterocyclyl, aryl, heteroaryl, halo (e.g., F, Cl, Br, or I), —OR', —NR'R", —CF$_3$, —CN, —NO$_2$, —C$_2$R', —SR', —N$_3$, —C(C=O)NR'R", —NR'C(=O) R", —C(=O)R', —C(=O)OR', —OC(=O) R', —OC(=O)NR'R", —NR'C(=O)OR", —SO$_2$R', —SO$_2$NR'R", and —NR'SO$_2$R", j is a whole number from 0 to 3.

Representative compounds falling within the scope of Formula 1 include

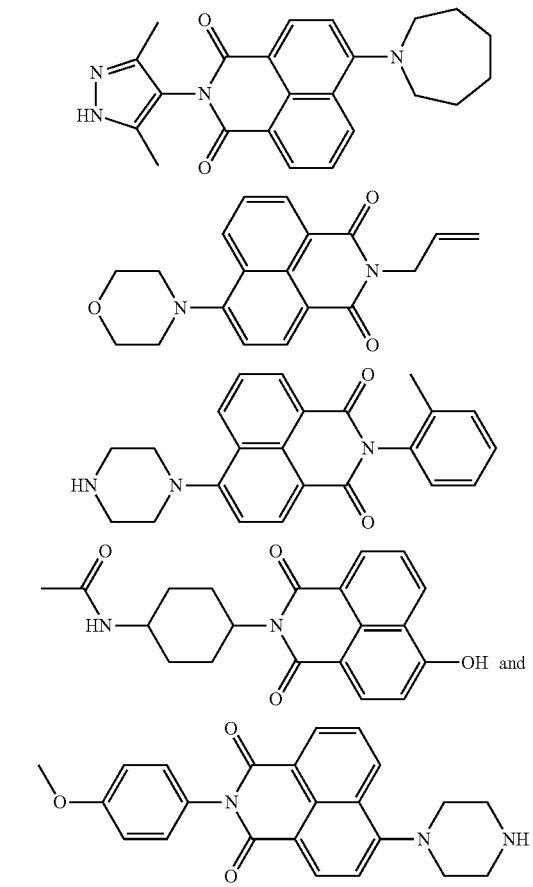

and analogs of these compounds, in which one or more of the aromatic rings is substituted with one or more substituents, Z.

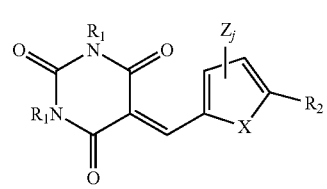

Formula 2 wherein $R_1$, $R_2$, Z and j are as defined above with respect to Formula 1, and X is O, S, or $NR_1$. Specific R1 moieties include includes $C_{5-7}$ azacyclic rings, such as azepane, $C_{5-7}$ azacyclic rings that further include an oxygen atom, such as morpholine, and $C_{5-7}$ azacyclic rings that include two ring nitrogen atoms, such as piperazine. Representative compounds falling within the scope of Formula 2 are shown below:

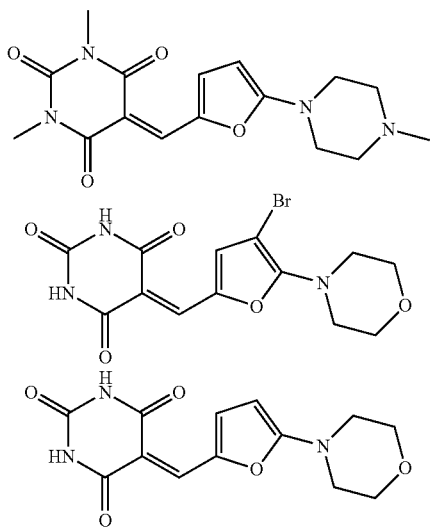

and analogs of these compounds, in which the furan ring is substituted with one or two substituents, Z.

Formula 3

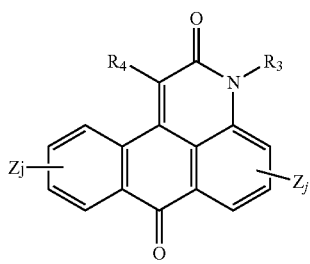

wherein Z, j, are as defined above with respect to Formula 1, $R_3$ is H, $C_{1-6}$ alkyl, $C_{3-10}$ cycloalkyl, $C_{2-6}$ alkenyl, aryl, heteroaryl, and heterocyclyl, and $R_4$ is $NHR_1$ or heterocyclyl, specifically including $C_{5-7}$ azacyclic rings, such as azepane, $C_{5-7}$ azacyclic rings that further include an oxygen atom, such as morpholine, and $C_{5-7}$ azacyclic rings that include two ring nitrogen atoms, such as piperazine, more specifically, wherein the link to the core structure is through a nitrogen atom on the azacyclic ring.

Specific compounds within the scope of Formula 3 include the following:

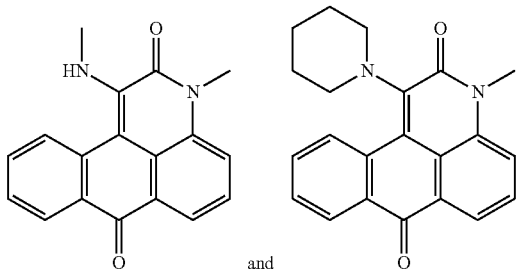 [SMILES: CNc1c2c3c(cccc3n(C)c1=O)C(=O)c1ccccc1-2 ; Cn1c(=O)c(N2CCCCC2)c2c3c(cccc31)C(=O)c1ccccc1-2]

and analogs of these compounds, in which one or both of the aromatic rings are substituted with one or two substituents, Z.

Formula 4

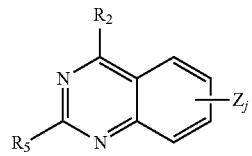

wherein $R_2$, Z, and j are as defined above with respect to Formula 1, and $R_5$ is H, $NHR_1$, wherein $R_1$ specifically includes optionally substituted pyrimidine, dihydropyrimidine, and hexahydropyrimidine rings, aryl, styrenyl, wherein the aryl rings can be substituted with one or more substituents, Z, and wherein at least one of $R_2$ and $R_5$ is $NHR_1$ or a $C_{5-7}$ azacyclic rings, such as azepane, $C_{5-7}$ azacyclic rings that further include an oxygen atom, such as morpholine, and $C_{5-7}$ azacyclic rings that include two ring nitrogen atoms, such as piperazine, and, more specifically, wherein the link to the core structure is through a nitrogen atom on the azacyclic ring.

Representative compounds falling within the scope of FIG. 4 include:

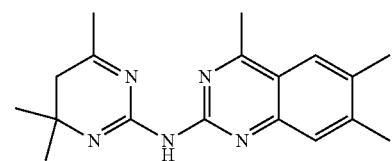

and analogs thereof wherein the aromatic ring is substituted with from one to three substituents, Z.

Formula 5

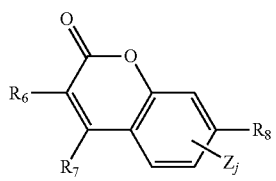

wherein Z and j are as defined above with respect to Formula 1, $R_6$ is aryl, heteroaryl, specifically including benzooxazol2-yl, and benzythiazol-2-yl, $R_7$ is H, $C_{1-6}$ alkyl, aryl, or heteroaryl, including 5 and 6-membered heteroaryl rings, such as pyridine, pyrimidine, pyrazine, imidazole, pyrazole, thiophene, pyrrole, and furan, $R_8$ is $OR_1$, $SR_1$, $N(R_1)_2$, specifically including OH, methoxy, diethylamino, and —O—CH(Aryl)-C(O)$OR_1$;

wherein $R_6$ and $R_7$ can optionally combine to form a benzene substituent (i.e., forming a benzo[c]chromene moiety), and wherein the Z substituents specifically include $C_{1-6}$ alkyl and an optionally substituted —$CH_2$—$C_{5-7}$ azacycle, where the azacycle is optionally linked to the —$CH_2$-moiety via the ring nitrogen.

Specific compounds falling within the scope of Formula 5 include:

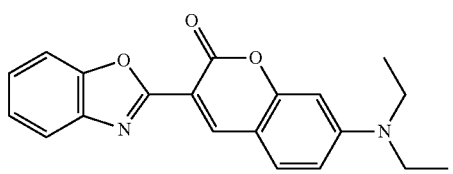

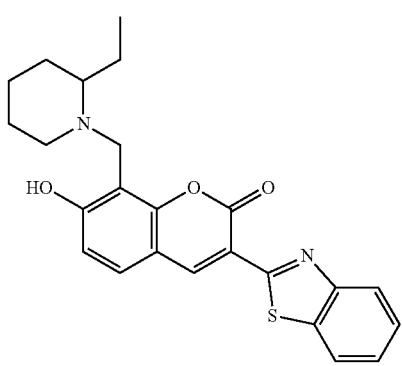

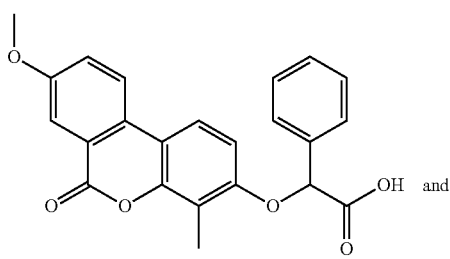

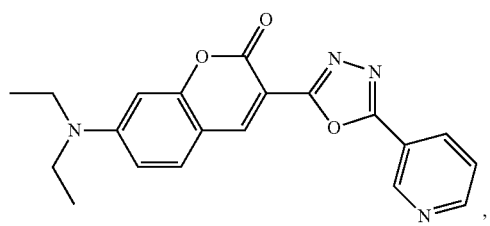

and analogs of these compounds, in which one or more of the aromatic or heteroaromatic rings is substituted with one or two substituents, Z.

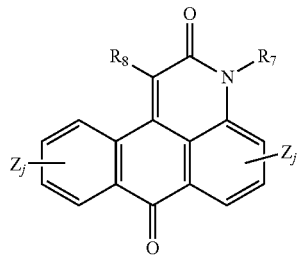

Formula 6 wherein $R_1$, Z and j are as defined above with respect to Formula 1, R7 is as defined above with respect to Formula 5, and $R_8$ is $NHR_1$ or a $C_{5-7}$ azacyclic rings, such as azepane, $C_{5-7}$ azacyclic rings that further include an oxygen atom, such as morpholine, and $C_{5-7}$ azacyclic rings that include two ring nitrogen atoms, such as piperazine, and, more specifically, wherein the link to the core structure is through a nitrogen atom on the azacyclic ring.

Specific compounds within the scope of Formula 6 include:

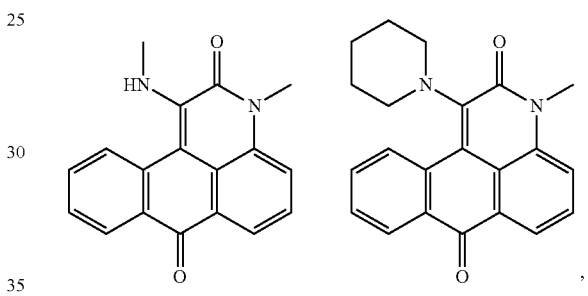

and analogs of these compounds, in which one or more of the aromatic rings is substituted with one or two substituents, Z.

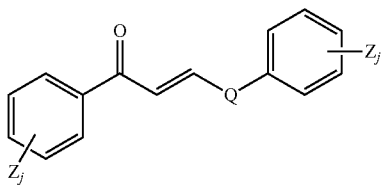

Formula 7 where $R_1$, Z and j are as defined with respect to Formula 1, and specifically include H, OH, vinyl, and dialkylamine, such as diethylamine, and Q is either a direct link, an —O—, —S—, or an —$NR_1$— moiety.

Representative compounds falling within the scope of Formula 7 include:

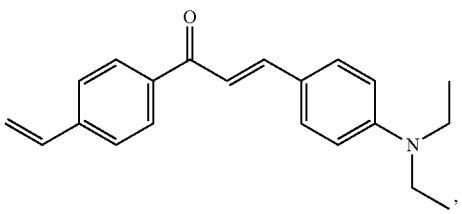

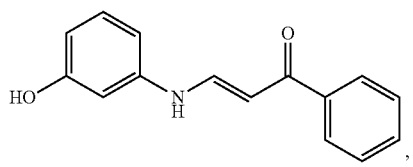

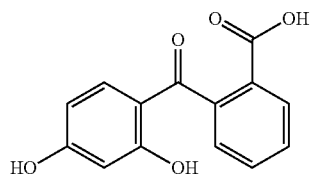

and analogs of these compounds, in which one or more of the aromatic rings is substituted with one or two substituents, Z.

and analogs of this compound, in which the aromatic ring is substituted with one or two substituents, Z.

Formula 8

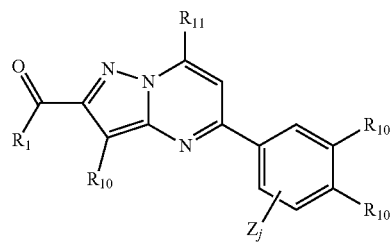

Formula 10

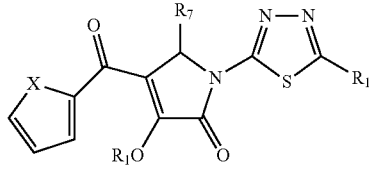

wherein $R_1$ is as defined with respect to Formula 1, $R_7$ is as defined with respect to Formula 5, and X is as defined with respect to Formula 2.

Specific compounds falling within the scope of Formula 10 are shown below:

wherein $R_1$, Z, and j are as defined with respect to Formula 1, $R_{10}$ is, independently, halogen (including F, Cl, Br, and I), $OR_1$, $SR_1$, $NHR_1$, —CN, or azido, and $R_{11}$ is $C_{1-6}$ alkyl or $C_{1-6}$ haloalkyl, such as trifluoromethyl.

A specific compound falling within Formula 8 is shown below:

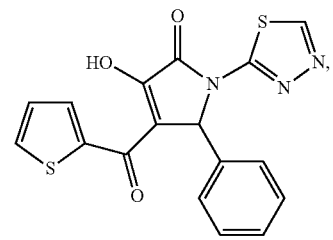

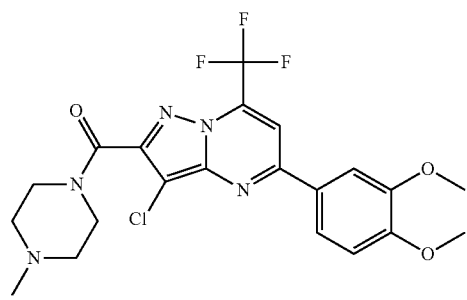 [SMILES: COc1ccc(-c2cc(C(F)(F)F)n3nc(C(=O)N4CCN(C)CC4)c(Cl)c3n2)cc1OC]

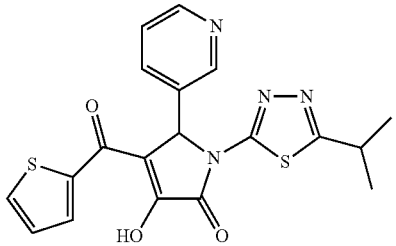

and analogs of these compounds, in which the aryl or heteroaryl ring is substituted with one or two substituents, Z.

Additional active compounds were identified, but did not fall within any of the general formulas shown above. A complete list of active compounds identified in the high throughput screening assay is shown below.

and analogs of this compound, in which the aromatic ring is substituted with one or two substituents, Z.

Formula 9

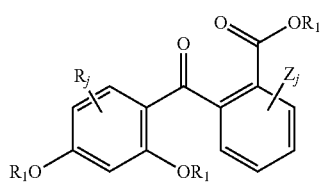

Wherein Z, j, and $R_1$ are as defined with respect to Formula 1. A representative compound falling within the scope of Formula 9 is shown below:

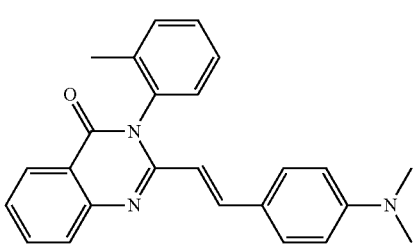

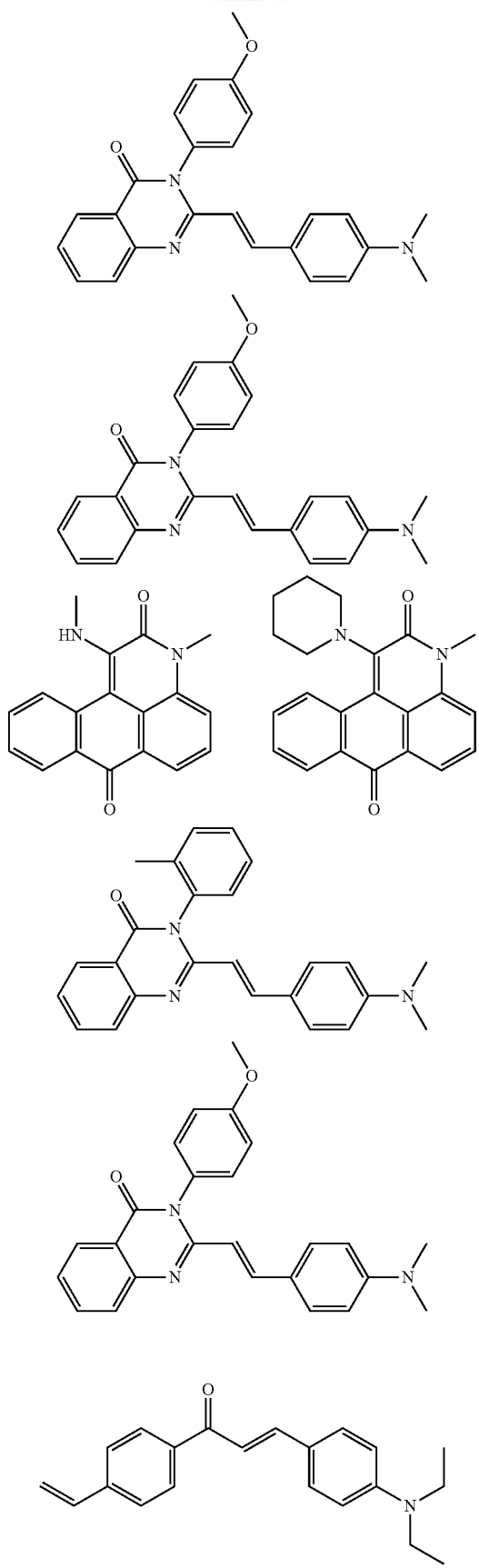
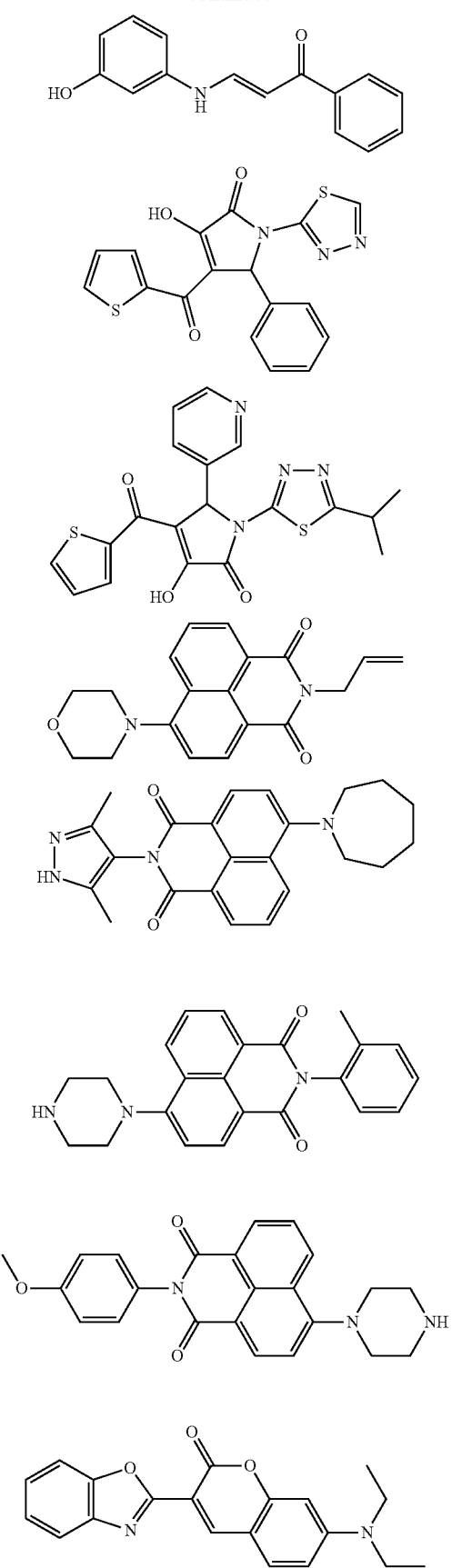

33
-continued
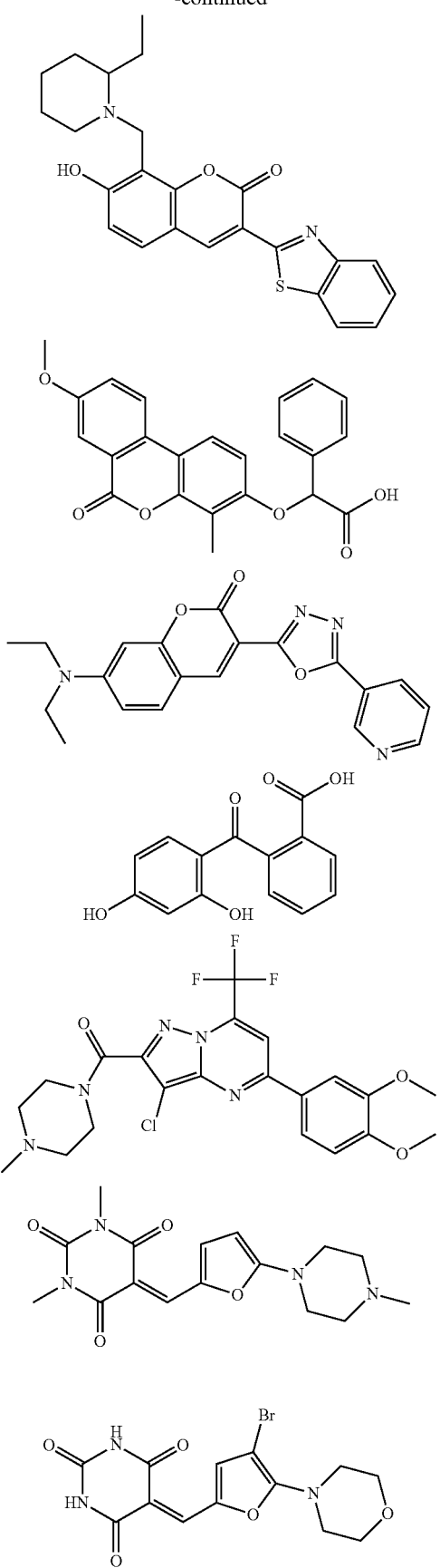
34
-continued
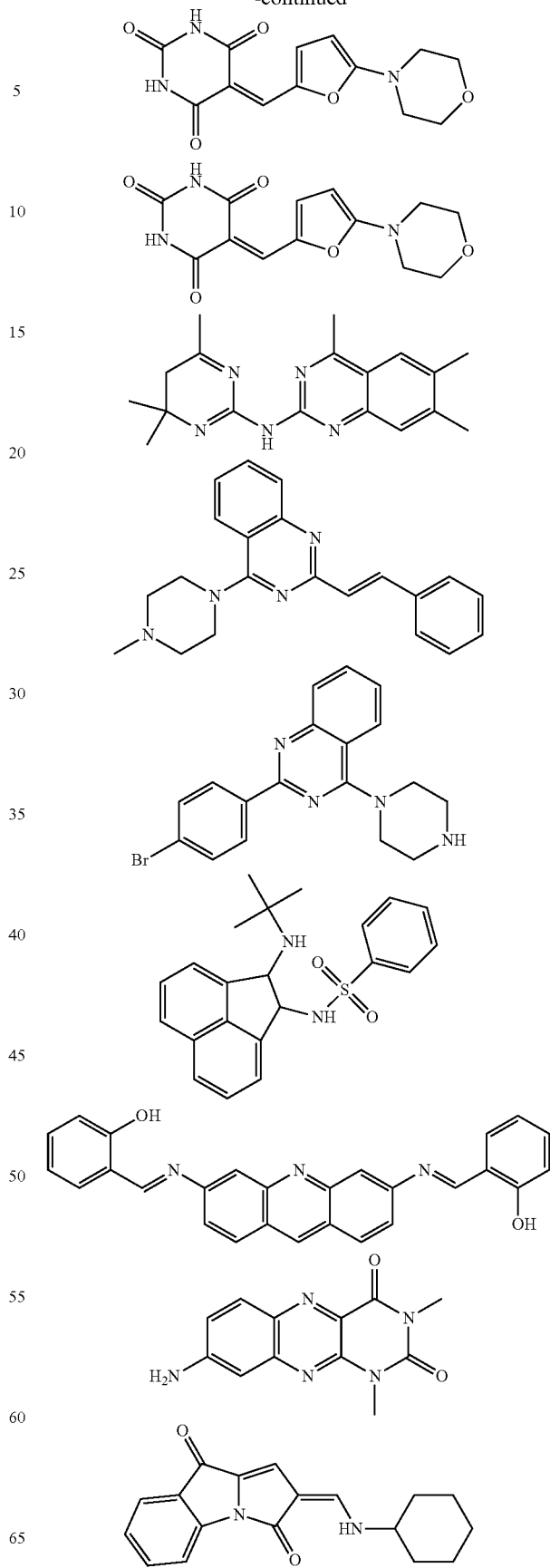

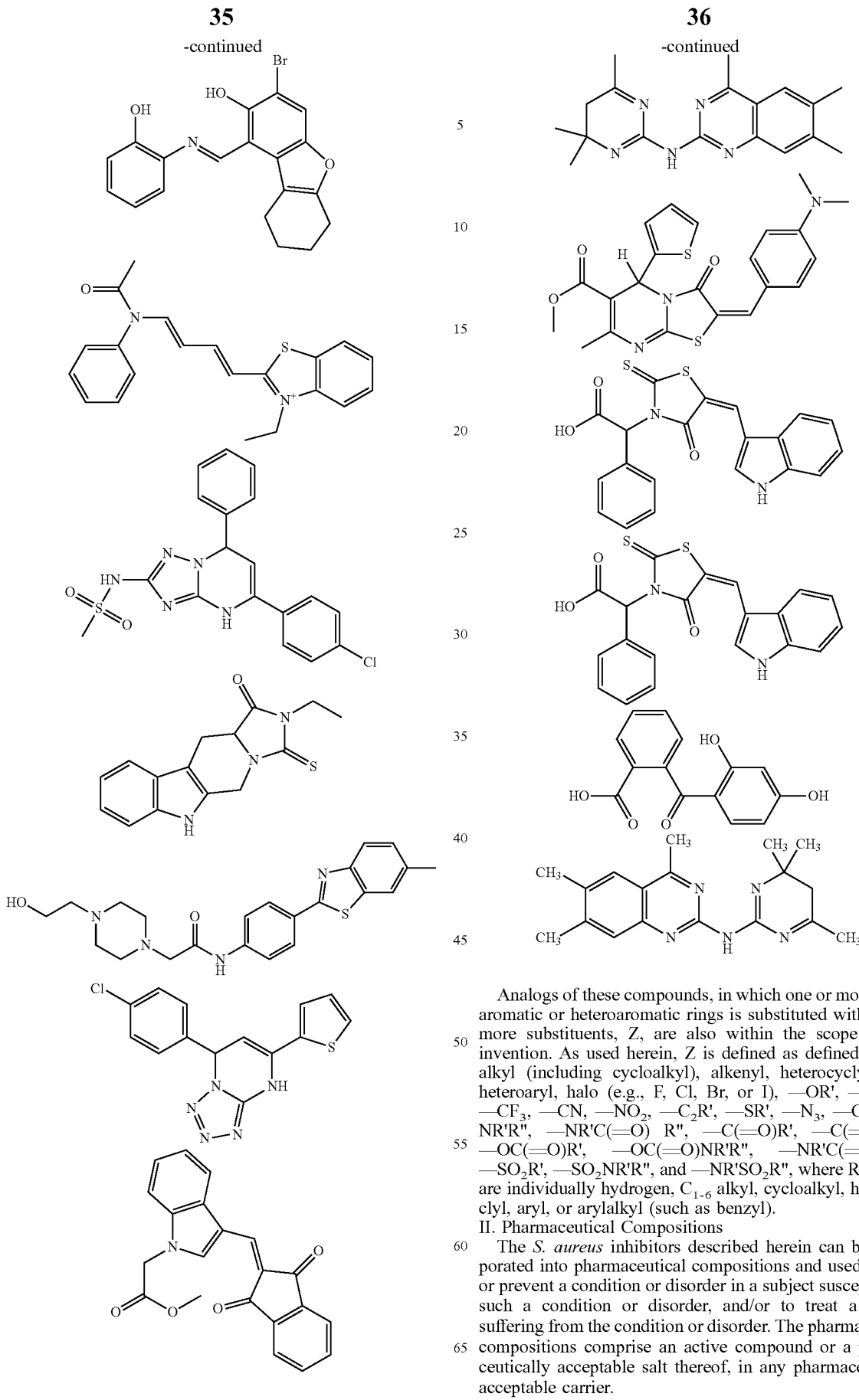

Analogs of these compounds, in which one or more of the aromatic or heteroaromatic rings is substituted with one or more substituents, Z, are also within the scope of this invention. As used herein, Z is defined as defined as $C_{1-6}$ alkyl (including cycloalkyl), alkenyl, heterocyclyl, aryl, heteroaryl, halo (e.g., F, Cl, Br, or I), —OR', —NR'R", —CF$_3$, —CN, —NO$_2$, —C$_2$R', —SR', —N$_3$, —C(C=O)NR'R", —NR'C(=O) R", —C(=O)R', —C(=O)OR', —OC(=O)R', —OC(=O)NR'R", —NR'C(=O)OR", —SO$_2$R', —SO$_2$NR'R", and —NR'SO$_2$R", where R' and R" are individually hydrogen, $C_{1-6}$ alkyl, cycloalkyl, heterocyclyl, aryl, or arylalkyl (such as benzyl).

II. Pharmaceutical Compositions

The *S. aureus* inhibitors described herein can be incorporated into pharmaceutical compositions and used to treat or prevent a condition or disorder in a subject susceptible to such a condition or disorder, and/or to treat a subject suffering from the condition or disorder. The pharmaceutical compositions comprise an active compound or a pharmaceutically acceptable salt thereof, in any pharmaceutically acceptable carrier.

Optically active compounds can be employed as racemic mixtures, as pure enantiomers, or as compounds of varying enantiomeric purity. The pharmaceutical compositions described herein include the inhibitors and a pharmaceutically acceptable carrier and/or excipient.

The manner in which the compounds are administered can vary. The compositions are preferably administered orally (e.g., in liquid form within a solvent such as an aqueous or non-aqueous liquid, or within a solid carrier). Preferred compositions for oral administration include pills, tablets, capsules, caplets, syrups, and solutions, including hard gelatin capsules and time-release capsules. Compositions may be formulated in unit dose form, or in multiple or subunit doses. Preferred compositions are in liquid or semisolid form. Compositions including a liquid pharmaceutically inert carrier such as water or other pharmaceutically compatible liquids or semisolids may be used. The use of such liquids and semisolids is well known to those of skill in the art.

The compositions can also be administered via injection, i.e., intraveneously, intramuscularly, subcutaneously, intraperitoneally, intraarterially, intrathecally; and intracerebroventricularly. Intravenous administration is a preferred method of injection. Suitable carriers for injection are well known to those of skill in the art, and include 5% dextrose solutions, saline, and phosphate buffered saline. The compounds can also be administered as an infusion or injection (e.g., as a suspension or as an emulsion in a pharmaceutically acceptable liquid or mixture of liquids).

If a solution is desired, water is the carrier of choice with respect to water-soluble compounds or salts. With respect to the water-insoluble compounds or salts, an organic vehicle, such as glycerol, propylene glycol, polyethylene glycol, or mixtures thereof, may be suitable. In the latter instance, the organic vehicle may contain a substantial amount of water. The solution in either instance may then be sterilized in any suitable manner, preferably by filtration through a 0.22 micron filter. Subsequent to sterilization, the solution may be filled into appropriate receptacles, such as depyrogenated glass vials. Of course, the filling should be done by an aseptic method. Sterilized closures may then be placed on the vials and, if desired, the vial contents may be lyophilized.

In addition to active compounds or their salts, the pharmaceutical compositions may contain other additives, such as pH adjusting additives. In particular, useful pH adjusting agents include acids, such as hydrochloric acid, bases or buffers, such as sodium lactate, sodium acetate, sodium phosphate, sodium citrate, sodium borate, or sodium gluconate. Further, the compositions may contain anti-microbial agents. Useful antimicrobial agents include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

In yet another aspect of the present invention, there is provided an injectable, stable, sterile composition comprising an active compound or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into man. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

The formulations may also be administered using other means, for example, rectal administration. Formulations useful for rectal administration, such as suppositories, are well known to those of skill in the art. The compounds can also be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); or transdermally (e.g., using a transdermal patch, using technology that is commercially available from Novartis and Alza Corporation). Although it is possible to administer the compounds in the form of a bulk active chemical, it is preferred to present each compound in the form of a pharmaceutical composition or formulation for efficient and effective administration.

Other pharmaceutical compositions may be prepared from the active compounds, such as aqueous base emulsions. In such an instance, the composition will contain a sufficient amount of pharmaceutically acceptable emulsifying agent to emulsify the desired amount of the active compound or salt thereof. Particularly useful emulsifying agents include phosphatidyl cholines, and lecithin.

Further, the present invention provides liposomal formulations of the active compounds or salts thereof. The technology for forming liposomal suspensions is well known in the art. When the active compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Another type of delivery is by implantable drug delivery depots, which typically include a hydrophilic biocompatible, and optionally biodegradable polymer with the active agent physically contained within the structure. The active agent is released by its permeation of and diffusion through the polymer or copolymer structure. The depot may be designed to release the substance or substances at predetermined rates and in predetermined sequence. One type of depot system is of the kind disclosed in U.S. Pat. No. 4,450,150, in which the co-polymer is a poly(glutamic acid-co-ethyl glutamate) copolymer, which ultimately biodegrades to glutamic acid. Other suitable depot based drug delivery vehicles include polyethylene glycol, and copolymers thereof. Among the preferred configurations for the depots are rods and closed-end capsules.

Pharmaceutical formulations are also provided which are suitable for administration as an aerosol, by inhalation. These formulations comprise a solution or suspension of the desired active compound or a salt thereof or a plurality of solid particles of the compound or salt. The desired formulation may be placed in a small chamber and nebulized.

Nebulization may be accomplished by compressed air or by ultrasonic energy to form a plurality of liquid droplets or solid particles comprising the compounds or salts. The liquid droplets or solid particles should have a particle size in the range of about 0.5 to about 5 microns. The solid particles can be obtained by processing the compound, or a salt thereof, in any appropriate manner known in the art, such as by micronization. Most preferably, the size of the solid particles or droplets will be from about 1 to about 2 microns. In this respect, commercial nebulizers are available to achieve this purpose.

Preferably, when the pharmaceutical formulation suitable for administration as an aerosol is in the form of a liquid, the formulation will comprise a water-soluble active compound or a salt thereof, in a carrier which comprises water. A surfactant may be present which lowers the surface tension of the formulation sufficiently to result in the formation of droplets within the desired size range when subjected to nebulization.

Exemplary methods for administering such compounds will be apparent to the skilled artisan. The usefulness of these formulations may depend on the particular composition used and the particular subject receiving the treatment. These formulations may contain a liquid carrier that may be oily, aqueous, emulsified or contain certain solvents suitable to the mode of administration.

The compositions can be administered intermittently or at a gradual, continuous, constant or controlled rate to a warm-blooded animal (e.g., a mammal such as a mouse, rat, cat, rabbit, dog, pig, cow, or monkey), but advantageously are administered to a human being. In addition, the time of day and the number of times per day that the pharmaceutical formulation is administered can vary.

Preferably, the compositions are administered such that active ingredients interact with regions where microbial infections are located. The compounds described herein are very potent at treating these microbial infections.

In certain circumstances, the compounds described herein can be employed as part of a pharmaceutical composition with other compounds intended to prevent or treat a particular microbial infection, i.e., combination therapy. In addition to effective amounts of the compounds described herein, the pharmaceutical compositions can also include various other components as additives or adjuncts.

Combination Therapy

The combination therapy may be administered as (a) a single pharmaceutical composition which comprises an inhibitor as described herein, at least one additional pharmaceutical agent described herein, and a pharmaceutically acceptable excipient, diluent, depot, such as a polyethylene glycol depot, or carrier; or (b) two separate pharmaceutical compositions comprising (i) a first composition comprising an inhibitor as described herein and a pharmaceutically acceptable excipient, diluent, depot, or carrier, and (ii) a second composition comprising at least one additional pharmaceutical agent described herein and a pharmaceutically acceptable excipient, diluent, depot, or carrier. The pharmaceutical compositions can be administered simultaneously or sequentially and in any order.

In use in treating or preventing microbial disease, the inhibitors can be administered together with at least one other antimicrobial agent as part of a unitary pharmaceutical composition. Alternatively, it can be administered apart from the other antimicrobial agents. In this embodiment, the inhibitors and the at least one other antimicrobial agent are administered substantially simultaneously, i.e. the compounds are administered at the same time or one after the other, so long as the compounds reach therapeutic levels for a period of time in the blood.

Combination therapy involves administering the inhibitors, as described herein, in combination with at least one anti-microbial agent, ideally one which functions by a different mechanism (i.e., by penetrating the bacterial cell wall, or interfering with one or more receptors and/or enzymes in the bacteria).

Representative Antibacterial Compounds

Examples of antibacterial compounds include, but are not limited to, aminoglycosides, ansamycins, carbacephems, carbapenems, cephalosporins (First, Second, Third, Fourth and Fifth Generation), glycopeptides, macrolides, monobactams, penicillins and beta-lactam antibiotics, quinolones, sulfonamides, and tetracyclines.

Representative aminoglycosides include Amikacin, Gentamicin, Kanamycin, Neomycin, Netilmicin, Streptomycin, Tobramycin, and Paromomycin. Representative ansamycins include Geldanamycin and Herbimycin. These agents function by binding to the bacterial 30S or 50S ribosomal subunit, inhibiting the translocation of the peptidyl-tRNA from the A-site to the P-site and also causing misreading of mRNA, leaving the bacterium unable to synthesize proteins vital to its growth.

Loracarbef is a representative carbacephem. Representative carbapenems include Ertapenem, Doripenem, Imipenem/Cilastatin, and Meropenem.

Representative first generation cephalosporins include Cefadroxil, Cefazolin, Cephalothin, and Cephalexin. Representative second generation cephalosporins include Cefaclor, Cefamandole, Cefoxitin, Cefprozil, and Cefuroxime. Representative third generation cephalosporins include Cefixime, Cefdinir, Cefditoren, Cefoperazone, Cefotaxime, Cefpodoxime, Ceftazidime, Ceftibuten, Ceftizoxime, and Ceftriaxone. Cefepime is a representative fourth generation cephalosporin, and Ceftobiprole is a representative fifth generation cephalosporin.

Representative glycopeptides include Teicoplanin and Vancomycin, which function by inhibiting peptidoglycan synthesis.

Representative macrolides include Azithromycin, Clarithromycin, Dirithromycin, Erythromycin, Roxithromycin, Troleandomycin, Telithromycin, and Spectinomycin, which function by inhibiting bacterial protein biosynthesis by binding irreversibly to the subunit 50S of the bacterial ribosome, thereby inhibiting translocation of peptidyl tRNA.

Aztreonam is a representative monobactam.

Representative penicillins include Amoxicillin, Ampicillin, Azlocillin, Carbenicillin, Cloxacillin, Dicloxacillin, Flucloxacillin, Mezlocillin, Meticillin, Nafcillin, Oxacillin, Penicillin, Piperacillin, and Ticarcillin. These can be administered with an agent which inhibits beta-lactamase enzymatic activity, such as potassium clavanulate or clavulanic acid.

Representative quinolones include Ciprofloxacin, Enoxacin, Gatifloxacin, Levofloxacin, Lomefloxacin, Moxifloxacin, Norfloxacin, Ofloxacin, and Trovafloxacin.

Representative sulfonamides include Mafenide, Prontosil, Sulfacetamide, Sulfamethizole, Sulfanilimide, Sulfas alazine, Sulfisoxazole, Trimethoprim, and Trimethoprim-Sulfamethoxazole (Co-trimoxazole) (TMP-SMX).

Representative tetracyclines and tetracycline-like compounds include Glycylcycline class antibiotics such as Tigecycline; Demeclocycline, Doxycycline, Minocycline, Oxytetracycline, and Tetracycline.

Other antibacterial agents include, for example, Arsphenamine, Chloramphenicol, Clindamycin, Lincomycin, Ethambutol, Fosfomycin, Fusidic acid, Furazolidone, Isoniazid, Linezolid, Metronidazole, Mupirocin, Nitrofurantoin, Platensimycin, Pyrazinamide, Quinupristin/Dalfopristin, Rifampin or Rifampicin, and Tinidazole.

III. Methods of Using the Compounds and/or Pharmaceutical Compositions

The compounds can be used to treat or prevent microbial infections caused by Staphylococcus aureus. The compounds can also be used as adjunct therapy in combination with existing therapies in the management of the aforementioned types of infections. In such situations, it is preferably to administer the active ingredients to a patient in a manner that optimizes effects upon the Staphylococcus aureus bacteria, including drug resistant versions, while minimizing effects upon normal cell types. While this is primarily accomplished by virtue of the behavior of the compounds themselves, this can also be accomplished by targeted drug delivery and/or by adjusting the dosage such that a desired effect is obtained without meeting the threshold dosage required to achieve significant side effects.

S. aureus propagation can be inhibited by inhibiting ribosomal binding of a specific tRNA useful for incorporation of arginine into a growing peptide or protein in S. aureus, by an amount sufficient to inhibit S. aureus propagation. Inhibition of ribosomal binding may be carried out by contacting an active compound to the ribosome in an amount effective to inhibit binding sufficiently to inhibit S. aureus propagation. The S. aureus may be in vitro, in a culture media, or on a surface to be disinfected, or may be in vivo in a host (e.g., a human or animal host in need of an antimicrobial treatment). Formulations of active compounds can be prepared and administered in accordance with known techniques, as discussed below.

S. aureus propagation in a host can be inhibited by inhibiting the binding, or stabilizing the binding, of the specific host tRNA to the S. aureus RNA at one of the binding sites by an amount sufficient to inhibit propagation of the S. aureus in the host.

Formulations of active compounds can be prepared and administered in accordance with known techniques, as discussed below. In a preferred embodiment, the specific host tRNA is $tRNA^{Arg}$. Preferably the S. aureus primes translation specifically with the specific host tRNA, such as $tRNA^{arg}_{mnm5UCU}$. The host may be a cell in vitro, or a human or animal subject in need of such treatment.

Subjects to be treated by the methods of the present invention are typically human subjects, although the methods may be carried out with animal subjects (dogs, cats, horses, cattle, etc.) for veterinary purposes. The present invention provides pharmaceutical formulations comprising the active compounds, including pharmaceutically acceptable salts thereof, in pharmaceutically acceptable carriers for aerosol, oral, and parenteral administration as discussed in greater detail below. The therapeutically effective dosage of any specific compound, the use of which is in the scope of present invention, will vary somewhat from compound to compound, patient to patient, and will depend upon the condition of the patient and the route of delivery.

In accordance with the present method, an active compound or a pharmaceutically acceptable salt thereof, may be administered orally or through inhalation as a solid, or may be administered intramuscularly or intravenously as a solution, suspension, or emulsion. Alternatively, the compound or salt may also be administered by inhalation, intravenously or intramuscularly as a liposomal suspension. When administered through inhalation the active compound or salt should be in the form of a plurality of solid particles or droplets having a particle size from about 0.5 to about 5 microns, preferably from about 1 to about 2 microns.

The present invention will be better understood with reference to the following non-limiting examples.

EXAMPLE 1

Working Assay Protocol for TRANA SA 101 HTS Assay

The following is a general example of the screening assay described herein.
Assay Target: Ribosome of SA programmed with Arg message.
Assay tool: ASL of *S. aureus* tRNA Arg with FL label Sample detection method:—fluorescence quenching Sample format 96 and 384 well plates

- Sample volume: 100 μl and 5 μl
- Target concentration: 5 pM
- Tool concentration: 10 pM
- DMSO concentration 10%

Materials

- Isolated Ribosome (2 pM/μl)
- Message 2 ug/μl
- ASL 3-6 ug/μl
- CMN buffer—80 mM potassium cacodylate, pH 7.2, 20 mM $MgCl_2$, 100 mM $NH_4Cl$, and 3 mM β-mercaptoethanol Method—96 well format 1. Prepare programmed ribosome as follows:
   - a. Mix 5 pM per well,
   - b. 2 μg message
   - c. 0.3-10 pM ASL
   - d. 10 μl test compound
   - e. 100 μl volume
2. 20 min complex formation @ 37° C.
3. Read fluorescence on plate reader.

EXAMPLE 2

HTS Protocol to Identify Potential Inhibitors of *S. aureus*-derived Arg ASL RNA Oligomers with Ribosomes Introduction:

This assay was designed to identify inhibitors and agonists of *S. aureus* specific Arg ASL (anticodon stem loop) RNA oligomer interaction with programmed ribosomes, where inhibitors inhibit the complex formed between the ribosomes and the RNA oligomer and agonists stabilize the complex formed between the ribosomes and the RNA oligomer. The assay requires the following materials:

- Ribosomes—isolated from *E. coli* or *S. aureus*
- fMet tRNA (Sigma or Chemical Block, Moscow)
- mRNA (including the S-D sequence, the "box" sequence, the codon for methionine, and the codon for arginine that is specific for *S. aureus*, AGA, optionally with additional base pairs to the left of the S-D sequence and/or to the right of the codon for arginine)
- Fluorescently labeled Arg ASL oliogomer
- Buffer—$HAM_{20,\beta}$
- 384 well high binding micro titer plates (Matrix Technologies #4319, sold by Fischer Scientific as cat #50823855), or other appropriate plates for use in high throughput screening
- Filtration (Sartorius Stedium 100 Kdalton VC 1042) or centrifugation for complex purification EDTA—negative control (binding antagonist)

Neomycin—A-site binding enhancer (binding agonist)

Figure 11:
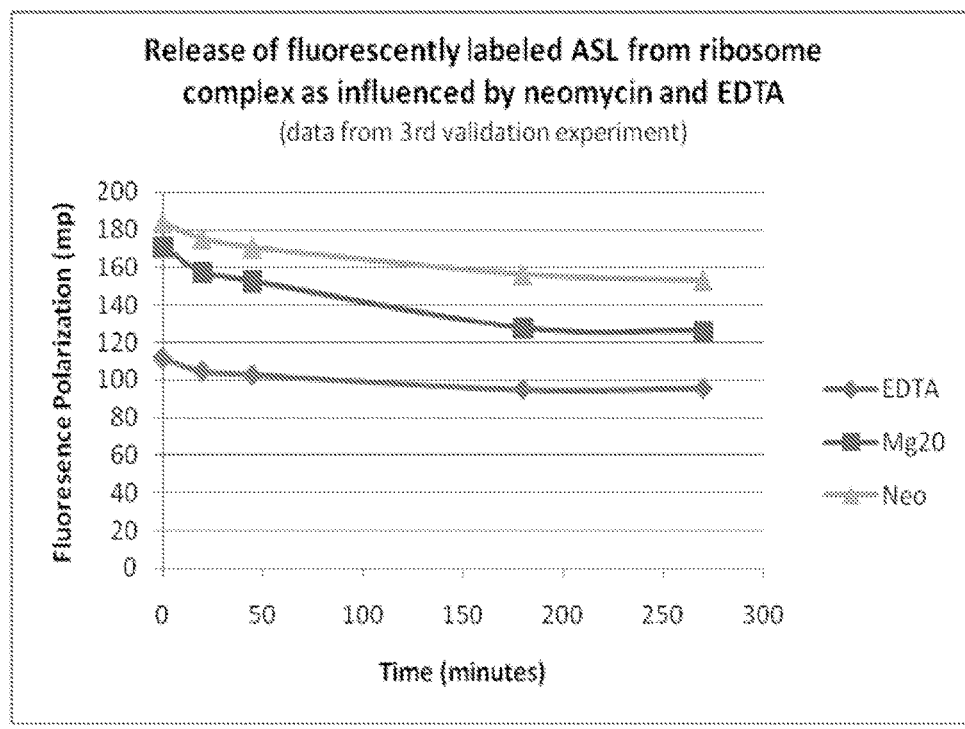
FIG. 11 is a chart showing the fluorescence polarization (mp) versus time (minutes). EDTA is shown as an inhibitor of complex formation, standard control (Mg20) is also shown, and neomycin (NEO) is shown as a stabilizer of complex formation.

A ribosome complex was prepared using the above materials and then purified prior to use in the assay. The prepared complex can be stored in concentrated form at −80° C. The complexes were diluted in buffer and dispensed onto plates. These complexes dissociate over time (control) and the dissociation rate is accelerated by potential inhibitors (inhibitors) or reduced by potential binding enhancers (agonist), both of which effectively inhibit protein synthesis. Fluorescence Polarization of Fluo-ASL bound to the ribosome was substantially higher than that of the free molecule, and therefore decreased upon complex dissociation (FIG. 11). Fluorescence polarization was measured at approximately 4 hours after dispensing onto the micro-titer plates.

Methods:

Preparation of Ribosomes:

Salt washed 70S ribosomes from Staph. aureus and E. coli cells were prepared according to Makhno V. I., Peshin N. N., Semenkov Y. P. and Kirillov S. V. (1988) Mol. Biol., 22, 528-537.

25 g frozen MRE600 E. coli cells (Cell Culture Facility, UAB) were re-suspended in 100 ml buffer A (20 mM Tris-HCl, pH7.5, 200 mM $NH_4Cl$, 20 mM $MgCl_2$, 3 mM b-mercaptoethanol), and passed through French press twice; cell debris was removed by 20 min centrifugation at 16,000 rpm in Beckman Ti 45 rotor. Crude ribosomes were collected by 3 h sedimentation at 3,000 rpm in the same rotor, dissolved in 75 ml 20 mM Tris-HCl, pH 7.5, 500 mM $NH_4Cl$, 10 mM $MgCl_2$, 3 mM β-mercaptoethanol, layered over 3×25 ml 1.1 M sucrose in the same buffer and spun in Ti 45 rotor overnight at 30,000 rpm. The pellet of salt washed 70S ribosomes was re-suspended in ~7 ml buffer A and stored at −80° C.

Staph. aureus cells were grown in the lab from Carolina Biological Supply Company culture and harvested when $A_{600}$ reached 0.6. On average, 8 g cells were obtained from 4×2 l cultures. Cells were re-suspended in 40 ml buffer A, and opened by sonication (3×30 sec). 70S ribosomes were purified as above.

fMet tRNA:

fMet tRNA was obtained commercially from Sigma for development studies and from Chemical Block for the validation studies and for use in the high throughput screening campaign.

mRNA Preparation:

The mRNA analog 5'-GGGCGAUAACACUCAGGA-GAUAAUAAAUGAGAACAGCUGAUCAAUCGUGCA UCC-3' was synthesized in vitro. Before addition to reaction 10 pm of single stranded DNA template GGATGCACGAT-TGATCAGCTGTTCTCATTTATTATCTCCTGAGTGT-TATCGCCCT ATAGTGAGTCGTATTA were annealed to 10 pm T7 DNA primer in 2 µl MEGAscript Kit (Ambion) reaction buffer for 5 min at 95° C. and 15 min at room temperature. Each standard 20 µl reaction was supplemented with additional 200µ of T7 polymerase and incubated overnight as recommended for short transcripts by the manufacturer. After DNase treatment mRNA was phenol extracted, ethanol precipitated twice and analyzed on 8% polyacrylamide gel for purity and stored in water. Approximately 400 nmol of mRNA were synthesized in 1 ml transcription reaction (=50×20 µl rxn/tube).

Preparation of (P+A) Complexes for the HTS Assay.

$ASL^{Arg}$ was first heated for 2 min at 90° C. in water, after addition of 1/10 V of 10× buffer incubation continued on ice for at least 10 min. Prior to complex formation 70S ribosomes and tRNA were reactivated in buffer for 5 min at 45° C. followed by 10 min at 37° C.; mRNA was heated in buffer at 37° C. for 5 min.

(1000 µl×(2 µM E. coli 70S ribosomes+10 µM mRNA-Arg+4 µM $tRNA^{fmet}$)/$HAM_{20,\beta}$→30 min @ 37° C.,+ 1000 µl×(0.2 µM neomycin+1 µM FITC-$ASL^{Arg}$))→20 min @ 37° C., overnight on ice Final complex: (2000 pm P+2000 pm ASL)/2 ml=1 µM P+1 µM ASL $HAM_{20,\beta}$:

50 mM HEPES-KOH, ph 7.5; 150 mm $NH_4Cl$; 200 mM $MgCl_2$; 3 mM β-mercaptoethanol Complex Purification—Filtration:

The complex was applied onto pre-washed Sartorius-100 filters, spun for 10 min @ 15000 g rcf, each filter was washed with 4×500 µl cold buffer×20 min @15000 g, and the volume of the concentrated sample was adjusted to max [P+A]~10 µM and stored either on ice if used immediately, or frozen at −80° C. if stored for later use.

Alternatively, these filters can be used with air pressure rather than centrifugation. In such a case, one can apply the complex onto pre-washed Vivaspin-20 filters, concentrate with air pressure to less than 200 µl, add buffer concentrate with air again, add buffer, and spin 20 min @ 2000 rpm in swinging rotor. This can be repeated with 2 more ml buffer. The final concentration can be adjusted, and the complex stored as above.

Complex Purification—Sedimentation Centrifugation:

For large scale purification 50 nm (P+A) complexes pre-incubated in 25 ml buffer were layered over 25 ml 1.1 m sucrose in $HAM_{20,\beta}$ buffer and spun for 4 hours at 40,000 rpm in Beckman Ti45 rotor (180,000×g at the bottom of the tube). The pelleted complexes free of unbound ligands were resuspended in 2.5 ml $HAM_{20,\beta}$ and stored as above.

Screening of Potential Inhibitors and Agonists:

Preparation of Complexes: The purified complex was diluted in ice cold $HAM_{20,\beta}$ such that the total fluorescence was approximately 2,000,000 units per 5 µL.

Preparation of 384 Well Plates: The assay was conducted in 22 plate batches due to logistic of plate preparation and analysis.

Control wells received 5 µl of either:

10% DMSO/$HAM_{20}$; and 0.5 mM neomycin, 10% DMSO/$HAM_{20}$; or 15 mM EDTA, 10% DMSO/$HAM_{20}$.

Compound wells received 5 µl of compounds dissolved in 10% DMSO at nominal 20 mM final concentration.

Blank wells (16 wells in each plate) received 10% DMSO/$HAM_{20}$

Assay:

The library compound plates containing 1 mM compound stocks in 100% DMSO were thawed at room temperature for about 1 hr. The plates received $HAM_{20}$ buffer to achieve 100 µM compound concentration in 10% DMSO. The buffer was added by non-contact dispenser Multidrop NL. The plates were then shaken and the compounds are replicated (5 µL) into the assay plates using Biomek FX.

20 µl of the diluted complex was added to all 384 well plates (except for blank wells, which received 20 µL of $HAM_{20}$ only, without complex) using Multidrop dispenser after which the plates were incubated at 25° C. for 4 hours (target 4.5 hours for middle of batch). Plates were then analyzed for fluorescence polarization in Analyst HT fluorescence plate reader and the following instrument settings:

Excitation: 485 nm

Emission: 530 nm

Integration time 100 ms

The parallel and perpendicular fluorescence values of experimental wells were automatically corrected for the corresponding values obtained from the blank wells. The fluorescence polarization was calculated as following:

$$P=(I-Ip)/(I+Ip),$$

wherein Ip—is perpendicular fluorescence and I—is parallel fluorescence.

The percent of effect of experimental compounds was calculated as following:

$$\%\text{-}Inh=(P_0-Pc)/(P_0-P_{100})*100,$$

wherein $P_0$—is average polarization in 0%—inhibition control wells, $P_{100}$—is average polarization in 100%—inhibition control wells, and Pc—is polarization in compound well.

Data Analysis:

Z'-factors were calculated for all controls on each plate and used for quality control. In addition, heat maps are prepared for visual analysis of each plate. Data for the compounds was transformed for each plate using the buffer control as the baseline. Compounds that inhibit are presented and positive numbers and compounds that are agonistic are presented as negative numbers. Compounds that deviate greater than 3 standard deviations from the baseline control were selected for further analysis.

Validation Results:

Using the above described assay along with the improved quality control parameters, approximately 4,000 compounds (13 plates) were screened to determine if this assay could detect compounds that are potential inhibitors or agonists of the complex. The experiment was repeated on a second day to confirm the robustness and reproducibility of the assay when using an entirely new set of reagents. Finally to confirm that a single time point was sufficient, the plates were analyzed at approximately 3 and 4.5 hours.

The Z'-factors are presented in Table 1. Based on these results, only the 4.5 hour data were used in the selection of 'hits' described below. On Day 1, 1 plate had a Z'-factor for EDTA and 2 plates for neomycin that was below 0.4. On Day 2, excluding the 2 plates (98 and 99) with multi-drop pipettor errors, 4 plates had Z'-factors below 0.4 for neomycin and none for EDTA.

TABLE 1

Z'-factors for validation experiment across 13 plates/different days

Day 1

|  |  | 3 Hr. | 4.5 Hr. |
|---|---|---|---|
| 60000000000085 | EDTA | 0.472 | 0.693 |
| 60000000000086 | EDTA | 0.335 | 0.433 |
| 60000000000087 | EDTA | 0.33 | 0.522 |
| 60000000000088 | EDTA | 0.231 | 0.376 |
| 60000000000089 | EDTA | 0.525 | 0.683 |
| 60000000000090 | EDTA | 0.39 | 0.677 |
| 60000000000091 | EDTA | 0.467 | 0.57 |
| 60000000000092 | EDTA | 0.421 | 0.585 |
| 60000000000093 | EDTA | 0.204 | 0.453 |
| 60000000000094 | EDTA | 0.592 | 0.682 |
| 60000000000095 | EDTA | 0.294 | 0.595 |
| 60000000000096 | EDTA | 0.549 | 0.669 |
| 60000000000097 | EDTA | 0.532 | 0.628 |
| 60000000000085 | Neomycin | 0.62 | 0.561 |
| 60000000000086 | Neomycin | 0.529 | 0.647 |
| 60000000000087 | Neomycin | 0.513 | 0.525 |
| 60000000000088 | Neomycin | 0.588 | 0.579 |
| 60000000000089 | Neomycin | 0.66 | 0.614 |
| 60000000000090 | Neomycin | 0.416 | 0.595 |
| 60000000000091 | Neomycin | 0.488 | 0.346 |
| 60000000000092 | Neomycin | 0.495 | 0.532 |
| 60000000000093 | Neomycin | 0.495 | 0.524 |
| 60000000000094 | Neomycin | 0.439 | 0.377 |
| 60000000000095 | Neomycin | 0.52 | 0.447 |
| 60000000000096 | Neomycin | 0.575 | 0.653 |
| 60000000000097 | Neomycin | 0.463 | 0.475 |

Day 2

|  |  | 3 HR | 4.5 HR |
|---|---|---|---|
| 60000000000098 | EDTA | 0.34 | 0.59 |
| 60000000000099 | EDTA | −0.25 | −0.2 |
| 60000000000100 | EDTA | 0.24 | 0.43 |
| 60000000000101 | EDTA | 0.26 | 0.58 |
| 60000000000102 | EDTA | 0.36 | 0.53 |
| 60000000000103 | EDTA | 0.31 | 0.52 |
| 60000000000104 | EDTA | 0.3 | 0.47 |
| 60000000000105 | EDTA | 0.3 | 0.57 |
| 60000000000106 | EDTA | 0.27 | 0.4 |
| 60000000000107 | EDTA | 0.43 | 0.47 |
| 60000000000108 | EDTA | 0.48 | 0.54 |
| 60000000000109 | EDTA | 0.51 | 0.56 |
| 60000000000110 | EDTA | 0.46 | 0.59 |
| 60000000000098 | Neomycin | 0.49 | 0.37 |
| 60000000000099 | Neomycin | 0.37 | 0.37 |
| 60000000000100 | Neomycin | 0.16 | 0.52 |
| 60000000000101 | Neomycin | 0.46 | 0.51 |
| 60000000000102 | Neomycin | 0.33 | 0.3 |
| 60000000000103 | Neomycin | 0.52 | 0.51 |
| 60000000000104 | Neomycin | 0.44 | 0.48 |
| 60000000000105 | Neomycin | 0.56 | 0.49 |
| 60000000000106 | Neomycin | 0.45 | 0.21 |
| 60000000000107 | Neomycin | 0.65 | 0.74 |
| 60000000000108 | Neomycin | 0.53 | 0.43 |
| 60000000000109 | Neomycin | 0.42 | 0.33 |
| 60000000000110 | Neomycin | 0.33 | 0.34 |

*Plates 99 and 98 on Day 2 had multi-drop pipettor error and were discarded from analysis. No potential hits were identified on these 2 plates.

Analysis of Data for Potential Hits:

To identify potential hits, the data on each plate was converted to % of the buffer control i.e. 0%=buffer control. Those compounds with positive percent inhibition were identified as 'potential inhibitors' and those with negative percent control were identified as 'potential agonists'. And since this assay is evaluating a defined point in time rather than an absolute end-point the cutoff criteria for selecting potentially active compounds is based on 3 standard deviation or greater difference from the buffer control. Any inhibitors or agonists outside of this range would be more than 88% different than the buffer control and considered significant. If this cutoff produces too many hits, then a more stringent cutoff (more standard deviations) can be used.

As mentioned above, 2 plates on repeat had definite multi-drop pipettor error and were excluded from the day-to-day comparisons in the following discussion and fortunately none of the potential hits were on either of these plates. A summary of the potentially active compounds and a comparison between Day 1 and Day 2 are presented in and in Table 3. There were 17 and 17 potential inhibitors on Day 1 and 2, respectively, above the 3 standard deviation cutoff. Of these 8 were identified as potential hits on both days. The number of reproduced potential agonists was 5 when using just a little flexibility in the cutoff. Stated slightly different, there were 20 potential hits identified on both days for a hit rate of about 0.5% which is fairly typical for a biochemical assay and it is fairly typical for 50% of these to be reproduced.

These results clearly demonstrate a validated assay that can reproducibly identify potential hits.

TABLE 2

Summary of potential inhibitors.

| | Day 1 | | Day 2 | | |
|---|---|---|---|---|---|
| | Cutoff | # of potential hits | Cutoff | # of potential hits | # of reproduced hits |
| 3 sigma | 16.4 | 14 | 21.81 | 17 | 8 |
| 4 sigma | 22.9 | 7 | 29.60 | 9 | 6 |
| 5 sigma | 29.4 | 6 | 37.39 | 6 | 6 |
| 6 sigma | 35.9 | 6 | 45.18 | 5 | 6 |

TABLE 3

Summary of potential agonists.

| | Day 1 | | Day 2 | | |
|---|---|---|---|---|---|
| | Cutoff | # of potential hits | Cutoff | # of potential hits | # of reproduced hits |
| 3 sigma | −22.6 | 6 | −24.92 | 3 | 5* |
| 4 sigma | −29.1 | 1 | −32.70 | 3 | 3 |
| 5 sigma | −35.6 | 1 | −40.49 | 2 | 2 |
| 6 sigma | −42.1 | 1 | −48.28 | 2 | 1 |

*2 compounds were active on day 2, but just below the 3 standard deviation cutoff.

Selection of Compounds for IC$_{50}$ Analysis:

Overall, 59,444 compounds were tested during pilot and full scale HTS. The overall HTS statistics calculated across all compound samples were as following:

Average percent inhibition=−0.1%

Standard deviation=6.74%

3 sigma inhibition cut off=20.21

3 sigma activation cut off=−20.23

227 compounds inhibited complex formation greater than 20.21%

56 compounds activated complex formation grater than 20.23% (were below −20.23%)

All HTS hits passing the 3 sigma cut-off were selected for the follow up dose response study.

Selection of Compounds for Biological Activity Testing:

The 3 sigma HTS hits were cherry picked and retested in 6 pt dose response format, using 3× serial dilution and the top nominal concentration of 100 uM.

Protocol:

The compounds were serially diluted in 10% DMSO and plated into 384 well plates (in a volume of 5 μL) to achieve the nominal final concentration raging from 100 μM to 0.4 μM. The plates received 20 μl of the diluted complex following incubation at 25° C. for 4 hours. Plates were then analyzed for fluorescence polarization as described above (see HTS section).

In parallel, the compounds were tested for auto-fluorescence. To this end, the compounds were plated (using the same dilution protocol) into 384 well plates. The plates received 20 μL of the HAM$_{20}$ assay buffer only (without complex). The plates were incubated for 4 hrs and then were analyzed for fluorescence polarization as described above.

To provide correction for compound auto-fluorescence, the parallel and perpendicular fluorescence values in the presence of compound and complex were corrected for those in the presence of compound without complex. The corrected fluorescence values were used to calculate the polarization at each concentration of compound.

The compounds demonstrating dose-dependent effect on fluorescent polarization of the complex (after correction for auto-fluorescence) were selected for re-acquisition and for the follow up microbiological studies.

EXAMPLE 3

In Vivo Studies

A series of lead compounds identified in the in vitro screening were subjected to in vivo screening, to determine their effectiveness against *S. aureus*. The strains included *Staphylococcus aureus*, Methicillin Resistant (ATCC 33591), Methicillin-Resistant *Staphylococcus aureus* USA300, *Staphylococcus aureus* 158, *Staphylococcus aureus* 22, *Staphylococcus aureus* 2, *Staphylococcus aureus* (ATCC 29213), and *Staphylococcus aureus* 182. The majority of the compounds showed a minimum inhibitory concentration (MIC) of between 4 and 128 μg/ml, with one compound showing an MIC of 4-8 μg/ml for each strain that was tested.

The compounds were re-tested against other bacteria, including *Staphylococcus epidermidis* (ATCC 35984), *Staphylococcus epidermidis* (MRSE), *E. faecium* 134529, *E. faecium* 145494, *E. faecium* 29212, *E. faecium* 161651, *S. pneumoniae* 49619, and *S. pneumoniae* 149389.

In some cases, the compounds were as active, or nearly so, against the non-*S. aureus* bacterial strains. While not wishing to be bound to a particular theory, it is believed that these compounds function by stabilizing or inhibiting the complex between the mRNA Shine-Dalgarno sequence, and the anti-Shine Delgarno sequence in the ribosome, and inhibit protein translation in this manner, rather than by inhibiting the ASL Arg, and the codon encoding arginine (AGA), which is specific to *S. aureus*.

EXAMPLE 4

Evaluation of Compounds in Time-Kill Assays Against Drug-Resistant *S. aureus*

A series of compounds were evaluated for their activity against drug resistant *S. aureus*, including MSSA and MRSA strains. The data is shown below in Table 3, and the compounds shown in Table 3 are identified below.

Compound #169 is 2-[4-(2-hydroxyethyl)-1-piperazinyl]-N-[4-(6-methyl-1,3-benzothiazol-2-yl)phenyl]acetamide.

Compound #880 is 2-(4-bromophenyl)-4-(1-piperazinyl)-quinazoline.

Compound #096 is 4-(4-methyl-1-piperazinyl)-2-(2-phenylvinyl)quinazoline.

Compound #211 is [(8-methoxy-4-methyl-6-oxo-6H-benzo[c]chromen-3-yl)oxy](phenyl)acetic acid.

Compound #740 is 2-ethyl-3-thioxo-2,3,5,6,11,11a-hexahydro-1H-imidazo[1′,5′:1,6]pyrido[3,4-b]indol-1-one.

Compound #928 is 2-{4-[acetyl(phenyl)amino]-1,3-butadien-1-yl}-3-ethyl-1,3-benzothiazol-3-ium iodide.

Compound 537 is [5-(1H-indol-3-ylmethylene)-4-oxo-2-thioxo-1,3-thiazolidin-3-yl](phenyl)acetic acid.

Compound 136 is 3-bromo-1-{[(2-hydroxyphenyl)imino]methyl}-6,7,8,9-tetrahydrodibenzo[b,d]furan-2-ol.

TABLE 3

| Compound/Bacteria | 169 | 880 | 096 | 211 | 740 | 928 | 537 | 136 |
|---|---|---|---|---|---|---|---|---|
| IC$_{50}$ | 69.26 | 19.9 | 91.03 | weak agonist | 44.21 | strong agonist | strong agonist | 79.99 |
| MIC µg/ml | | | | | | | | |
| SA 33591 | 32 | 8 | >128 | >128 | 128 | 128 | 64 | 32 |
| SA USA 300 | 8 | 8 | 64 | 128 | 128 | 64 | 64 | 128 |
| SA 158 | 128 | 8 | 128 | 128 | 128 | 128 | 64 | 32 |
| SA 22 | 16 | 8 | 64 | 128 | 32 | 64 | 64 | 16 |
| SA 2 | 8 | 4 | 32 | 128 | 32 | 128 | 128 | 16 |
| SA 29213 | 16 | 8 | 64 | 128 | 64 | 64 | 64 | 32 |
| SA 182 | 16 | 8 | 128 | 128 | 128 | >128 | 64 | >128 |
| S. epidermidis 35984 | 16 | 8 | >128 | >128 | 128 | 128 | 128 | 64 |
| S. epidermidis MRSE 01 | 16 | 8 | 128 | >128 | 64 | 64 | 128 | 8 |
| E. faecium 134529 | 16 | 8 | 64 | >128 | 64 | 128 | 128 | 64 |
| E. faecium 145494 | 16 | 4 | 128 | >128 | >128 | 128 | >128 | >128 |
| E. faecalis 29212 | 64 | 8 | 128 | 128 | 128 | 128 | 128 | 128 |
| E. faecalis 161651 | 16 | 8 | 128 | 128 | 128 | 128 | 128 | 128 |
| S. pneumoniae 49619 | 64 | 32 | 64 | 32 | >128 | >128 | 32 | >128 |
| S. pneumoniae 149389 | 128 | 32 | 64 | 128 | >128 | >128 | 64 | >128 |
| E. coli 25922 | >128 | 64 | >128 | >128 | >128 | >128 | >128 | >128 |
| E. coli ESBL 4 | >128 | 64 | >128 | >128 | >128 | >128 | >128 | >128 |
| K. pneumoniae 700603 | >128 | >128 | >128 | >128 | >128 | >128 | >128 | >128 |
| K. pneumoniae UMM | >128 | >128 | >128 | >128 | >128 | >128 | >128 | >128 |
| Mammalian Cell Toxicity - CC$_{50}$ (ug/ml) | | | | | | | | |
| MRC5 | <2 | 2.18 | 62 | 26 | 62 | 20-64 | 38 | 6.8 |
| 3T3 | <2 | 2.11 | 51.5 | 28 | 20-64 | 20-64 | 20-64 | 2.3 |

The most active two compounds (#169 & 880) showed activity on all types of *S. aureus*, including vancomycin and methicillin resistant strains. They were not selective for only *S. aureus*, but were also broad spectrum for Gm (+) organisms (e.g. *Staph epi*, *E. faecium* and *E. faecalis*).

Two compounds (#880 and #169) were tested in time-kill assays against *S. aureus* strain 29213. These compounds were then used to attempt to select for resistant variants by passaging at sub-MIC concentrations for 20 passages.

Methods:

Time-Kill Experiments:

Twenty mL of MH-II media warmed to 37° C. was seeded with log-phase growth *S. aureus* strain 29213 at 1×10$^6$ cfu/mL in 50 mL erlenmeyer shake-flasks. Compound was added at 2× and 4× the MIC value. Negative controls (no drug) and positive drug controls (vancomycin at 2× and 4× the MIC) were included in the experiment. Flasks were shaken at 200 rpm and 37° C. Samples were taken at the times indicated (0, 2, 4, 6, 8 and 24 hrs post inoculation) and bacterial loads were quantified by limiting dilution assay.

Resistance Passaging Experiment:

The selected strain for this experiment was *S. aureus* ATCC 29213. A frozen glycerol stock was streaked onto MH-II agar and grown overnight at 37° C. The next day, 3-5 colonies were picked and grown in 3 mL of MH-II broth at 37° C. with 200 rpm shaking for approximately 4 hours. A 2-fold microdilution (in round-bottom, 96-well plates) was made for each compound being tested. CLSI guidelines for broth microdilution were followed. Using the bacteria grown from the overnight colonies, each microdilution was inoculated at a final concentration of 5×10$^5$ colony forming units (CFU)/mL. The microdilutions were incubated at 37° C. for 16 to 20 hours, after which the minimal inhibitory concentration (MIC) of each was read visually. The MIC is defined as the lowest concentration of compound resulting in no visible bacterial growth. This activity is recorded as the MIC at Passage 0. The contents of the well in the next dilution lower in concentration than the MIC (i.e., ½ the MIC) was mixed with a micropipette and 50 µL was transferred to 3 mL of fresh MH-II broth. This was grown at 37° C. with 200 rpm shaking for approximately 4 hours, at which time the sample was turbid. A 1 mL aliquot of this sample was added to a cryovial containing 300 µL of glycerol. This was marked as passage 1, vortexed, than placed in a −80° C. freezer for storage. The rest of the culture was adjusted to a bacterial concentration of 1×10$^6$cfu/mL (OD$_{600}$ of 0.004), which was then used to inoculate a microdilution of the same compound (final bacterial concentration of 5×10$^5$ cfu/mL). This was incubated at 37° C. for 16 to 20 hours. After that time the MIC was once again read and recorded as the MIC at Passage 1. This process was repeated through 20 passages. Ciprofloxacin was included as a control and an untreated sample was also passaged 20 times as a negative control.

Figure 12:
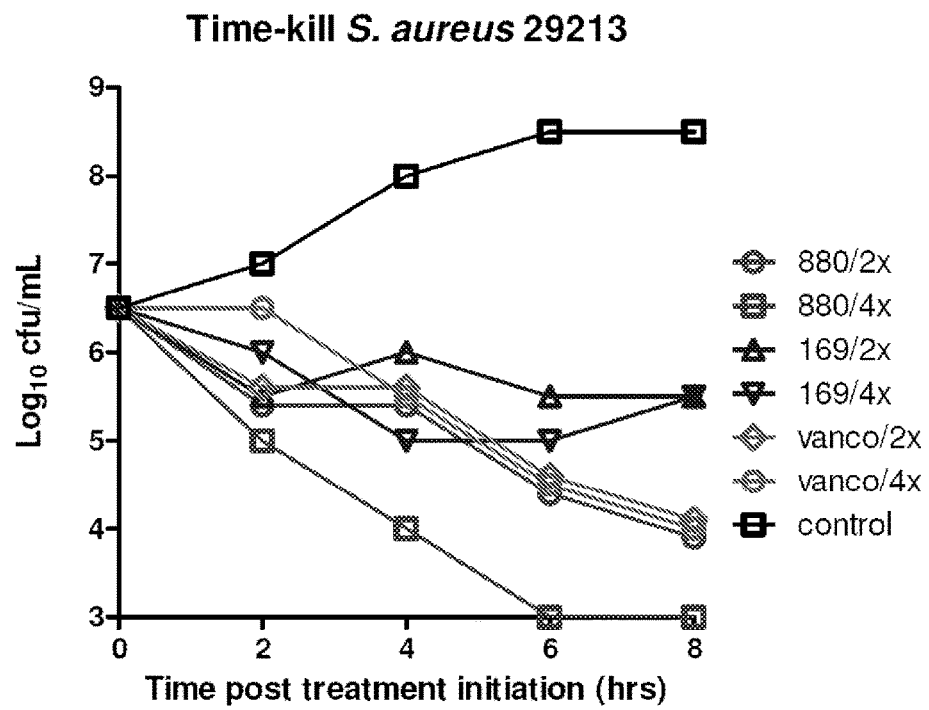
FIG. 12 is a chart showing the result of time-kill experimental results, over an eight hour time period, of S. aureus. The chart shows the effect of no treatment (control, shown in black squares), vancomycin at two times its minimum inhibitory concentration (MIC) value (green diamonds), vancomycin at four times its MIC (green circles), Compound #880 (2-(4-bromophenyl)-4-(1-piperazinyl)-quinazoline) at two times its MIC (red circles), Compound #880 at four times its MIC (red squares), Compound #169 (2-[4-(2-hydroxyethyl)-1-piperazinyl]-N-[4-(6-methyl-1,3-benzothiazol-2-yl)phenyl]acetamide) at two times its MIC (blue triangles), and Compound #169 at four times its MIC (upside down blue triangles), shown in terms of bacterial counts ($Log_{10}$ cFu/ml) over time (hours).

Results:

Time-kill experimental results through the 8 hr. time-point are shown in FIG. 12. The negative and positive control samples behaved as anticipated. Compound #880 was tested at 2× (16 µg/mL) and 4× (32 µg/mL) the MIC. Compound #169 was run at 32 and 64 µg/mL. As seen in this figure, compound #880 was rapidly cidal (>3 $\log_{10}$ killing) at 4× the MIC and reduced bacterial counts by 2.5 $\log_{10}$ at 2× the MIC. Compound #169 demonstrated static activity at both multiples of the MIC, with bacterial counts reduced by 1 $\text{Log}_{10}$ by 8 hours. Vancomycin reduced bacterial counts by 2.5 $\log_{10}$ at 2× and 4× its MIC value by 8 hours.

Figure 13:
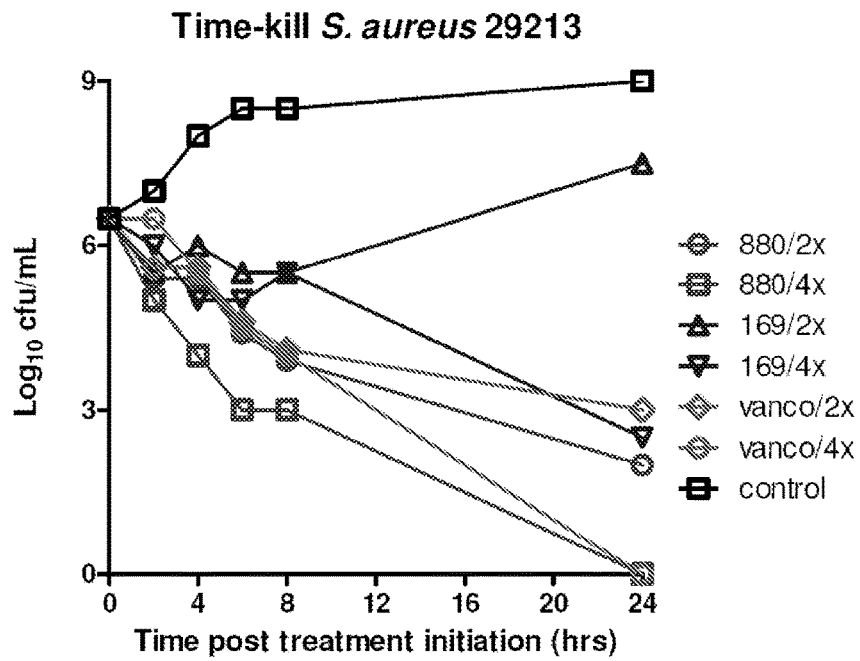
FIG. 13 is a chart showing the result of time-kill experimental results, over an eight hour time period, of S. aureus. The chart shows the effect of no treatment (control, shown in black squares), vancomycin at two times its minimum inhibitory concentration (MIC) value (green diamonds), vancomycin at four times its MIC (green circles), Compound #880 at two times its MIC (red circles), Compound #880 at four times its MIC (red squares), Compound #169 at two times its MIC (blue triangles), and Compound #169 at four times its MIC (upside down blue triangles), shown in terms of bacterial counts ($Log_{10}$ cFu/ml) over time (hours).

By 24 hrs post treatment, all treatments appeared to be cidal with the exception of #169 at 2× the MIC, which exhibited regrowth of bacteria. Compound #880 at 4× the MIC strikingly reduced bacterial counts to below detectable levels. The results are shown in FIG. 13.

Figure 14:
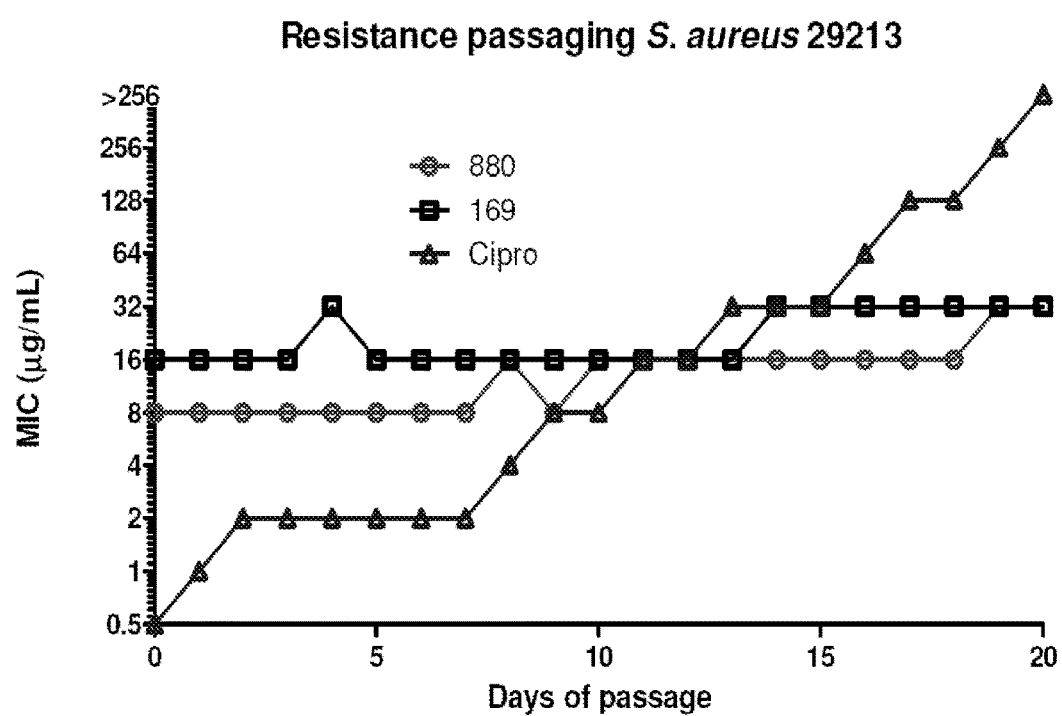
FIG. 14 is a chart showing the result of resistance selection experiments, using ciprofloxacin as a positive control (triangles), and evaluating Compound 880 (circles) and Compound 169 (squares), against S. aureus 29213, in terms of MIC (µg/ml) over time (days).

The 8-hr data suggested that the two compounds behaved in a somewhat different manner from one another, and these compounds were advanced to resistance selection experiments as described above. The results of 20 passages are shown in Table 4 and FIG. 14. Ciprofloxacin served as a positive control since it is known to select for resistance under passaging conditions such as those utilized herein. As shown below, treating the culture at a sub-MIC concentration of ciprofloxacin resulted in the MIC of the culture rising from 0.5 to >256 µg/mL (>512-fold) over 20 passages. By contrast, the MIC values for the two experimental compounds were essentially unchanged (i.e., MIC values within 1 dilution of untreated culture MIC values at passages 10 and 20) by passage 20.

TABLE 4

MIC (µg/ml) in *S. aureus* 29213

| Passage | 880 | 169 | Ciprofloxacin |
| --- | --- | --- | --- |
| 0 | 8 | 16 | 0.5 |
| 1 | 8 | 16 | 1 |
| 2 | 8 | 16 | 2 |
| 3 | 8 | 16 | 2 |
| 4 | 8 | 32 | 2 |
| 5 | 8 | 16 | 2 |
| 6 | 8 | 16 | 2 |
| 7 | 8 | 16 | 2 |
| 8 | 16 | 16 | 4 |
| 9 | 8 | 16 | 8 |
| 10 | 16 | 16 | 8 |
| 11 | 16 | 16 | 16 |
| 12 | 16 | 16 | 16 |
| 13 | 16 | 16 | 32 |
| 14 | 16 | 32 | 32 |
| 15 | 16 | 32 | 32 |
| 16 | 16 | 32 | 64 |
| 17 | 16 | 32 | 128 |
| 18 | 16 | 32 | 128 |
| 19 | 32 | 32 | 256 |
| 20 | 32 | 32 | >256 |
| 10 | 8 | 16 | 0.5 |
| 20 | 16 | 32 | 0.5 |

SUMMARY AND CONCLUSION

Time-kill experiments demonstrated that at 8 hrs #880 was rapidly cidal at 4× the MIC, while #169 appeared to be static. Attempts to select for resistant variants of these two experimental compounds by passaging did not result in an appreciable elevation in MIC values at passage 20. The control compound, ciprofloxacin, increased its MIC by >512-fold under these passaging conditions.

LITERATURE CITED

The following references were cited herein, and the contents of these references, and all other references cited herein, are hereby incorporated by reference in their entirety.

Agris P F. Decoding the genome: a modified view. Nucleic Acids Res. 2004 January 9; 32(1):223-38.

Agris P F, Malkiewicz A, Kraszewski A, Everett K, Nawrot B, Sochacka E, Jankowska J, Guenther R. Biochimie. (1995) Site-selected introduction of modified purine and pyrimidine ribonucleotides into RNA by automated phosphoramidite chemistry. 77(1-2): 125-34.

Agris P F, Guenther R, Ingram P C, Basti M M, Stuart J W, Sochacka E, Malkiewicz A. (1997) Unconventional structure of tRNA(Lys)SUU anticodon explains tRNA's role in bacterial and mammalian ribosomal frameshifting and primer selection by HIV-1. RNA. 1997 April; 3(4):420-8.

Agris P F, Guenther R, Sochacka E, Newman W, Czerwinska G, Liu G, Ye W, Malkiewicz A. (1999) Thermodynamic contribution of nucleotide modifications to yeast tRNA(Phe) anticodon stem loop analogs. Acta Biochim Pol. 1999; 46(1):163-72.

Ashraf S, Sochacka E, Cain R, Guenther R, Malkiewicz A, Agris P F. RNA (1999) Single atom modification (O->S) of tRNA confers ribosome binding. (2):188-94.

Ashraf S, Ansari G, Guenther R, Sochacka E, Malkiewicz A, Agris P F. (1999) The uridine in "U-turn": contributions to tRNA-ribosomal binding. RNA. 1999 April; 5(4):503-11.

CDC 2000-2001. "Drug Resistance/Antimicrobial Resistance", Centers for Disease Control and Prevention, CDC Fact Book 2000/2001, p. 75.

DRAGON. http://www.disat.unimib.it/chm/Dragon.htm. 2005. Ref Type: Electronic Citation Francois B, Russell R J, Murray J B, Aboul-ela F, Masquida B, Vicens Q, Westhof E. *Nucleic Acids Res.* (2005) Crystal structures of complexes between aminoglycosides and decoding A site oligonucleotides: role of the number of rings and positive charges in the specific binding leading to miscoding. 33 (17):5677-90.

Grosjean, H. and Benne, R. Modification and editing of RNA. Washington, D.C.: ASM Press, c1998.

Hermann T. *Curr Opin Struct Biol.* (2005) Drugs targeting the ribosome. 15(3):355-66.

Kumar R K, Davis DR. Synthesis and studies on the effect of 2-thiouridine and 4-thiouridine on sugar conformation and RNA duplex stability. Nucleic Acids Res. 1997 March 15; 25(6):1272-80.

Limbach, P. A., P. F. Crain and J. A. McCloskey. Summary: the modified nucleotides of RNA. *Nucleic Acids Res.* 22, 2183-2196 (1994).

Malkiewicz, A. and E. Sochacka 1983 The protected derivatives of 5-methylaminomethyl-2-thiouridine and 5-carbomethoxymethyl-2-thiouridine as components for the oligonucleotide synthesis. Tetrahedron Letters 24, 5387-5390.

Murphy F V 4th, Ramakrishnan V, Malkiewicz A, Agris P F. *Nat Struct Mol Biol.* (2004) The role of modifications in codon discrimination by tRNA(Lys)UUU. (12):1186-91.

Nobles K N, Yarian C S, Liu G, Guenther R H, Agris P F. (2002) Highly conserved modified nucleosides influence Mg2+-dependent tRNA folding. Nucleic Acids Res. 30:4751-60.

Ogilvie K, Usman N, Nicoghosian K, Cedergren R J. 1988 Total chemical synthesis of a 77-nucleotide-long RNA sequence having methionine-acceptance activity. Proc Natl Acad Sci USA. 85:5764-8

Phelps S, Malkiewicz A, Agris P F, Joseph S. *J Mol Biol.* (2004) Modified nucleotides in tRNA(Lys) and tRNA(Val) are important for translocation 338(3):439-44.

PubChem. http://pubchem.ncbi.nlm.nih.gov/ 2008. Ref Type: Electronic Citation

Ryszard W. Adamiak and Jacek Stawinski, 1977. A highly effective route to N,N'-disubstituted ureas under mild conditions. an application to the synthesis of tRNA anticodon loop fragments containing ureidonucleosides. Tetrahedron Letters, 18: 1935-1936.

Schilling-Bartetzko S, Franceschi F, Sternbach H, Nierhaus K H. Apparent association constants of tRNAs for the ribosomal A, P, and E Sites. J Biol Chem. 1992 March 5; 267(7):4693-702.

Soll, D. and RajBhandary, U. L. tRNA: structure, biosynthesis, and function. ASM Press, c1995.

Stuart J W, Gdaniec Z, Guenther R, Marszalek M, Sochacka E, Malkiewicz A, Agris P F. (2000). Functional anticodon architecture of human tRNALys3 includes disruption of intraloop hydrogen bonding by the naturally occurring amino acid modification, t6A. Biochemistry. 39:13396-404.

Sundaram M, Crain P F, Davis DR. 2000. Synthesis and characterization of the native anticodon domain of E. coli tRNA(Lys): simultaneous incorporation of modified nucleosides mnm(5)s(2)U, t(6)A, and pseudouridine using phosphoramidite chemistry. J Org Chem.65:5609-14.

Tropsha, A, Golbraikh, A. 2007. Predictive QSAR Modeling Workflow, Model Applicability Domains, and Virtual Screening. *Curr. Pharm. Des.* 13: 3494-504 von Ahsen U, Green R, Schroeder R, Noller H F. Identification of 2'-hydroxyl groups required for interaction of a tRNA anticodon stem-loop region with the ribosome. RNA. 1997 January; 3(1):49-56.

Wells B D, Cantor CR. 1980. Ribosome binding by tRNAs with fluorescent labeled 3' termini. Nucleic Acids Res. 1980 July 25; 8(14):3229-46.

Yarian C, Townsend H, Czestkowski W, Sochacka E, Malkiewicz A J, Guenther R, Miskiewicz A, Agris P F. *J Biol Chem*. (2002) Accurate translation of the genetic code depends on tRNA modified nucleotides. 277(19):16391-5.

Zhang J. H., Chung T. D. Y., Oldenburg, K. R J. *Biomol. Screen* (1999) A simple statistical parameter for use in the evaluation and validation of high throughput screening assays. 4, 67-73.

Zhang R, Ou H Y, Zhang C T. Nucleic Acids Res. 2004 January 1; 32(Database issue):D271-2. DEG: a database of essential genes.

Although the foregoing invention has been described in some detail by way of illustration and example for purposes of clarity of understanding, it will be obvious that certain changes and modifications may be practiced within the scope of the appended claims.

The invention claimed is:

1. A method of specifically treating a *Staphylococcus* infection, while not significantly inhibiting the propagation of bacteria which do not use AGA as a codon for translation of arginine, comprising administering a compound selected from the group consisting of:

2-[2-(4-Dimethylamino-phenyl)-vinyl]-3-(4-methoxy-phenyl)-3H-quinazolin-4-one,

2-[2-(4-Dimethylamino-phenyl)-vinyl]-3-o-tolyl-3H-quinazolin-4-one, 4-(4-Methyl-piperazin-1-yl)-2-styryl-quinazoline, and 2-(4-Bromo-phenyl)-4-piperazin-1-yl-quinazoline, wherein any of the aromatic rings in these compounds can be optionally substituted with one or more substituents, Z, wherein Z is defined as $C_{1-6}$ alkyl, alkenyl, heterocyclyl, aryl, heteroaryl, halo, —OR', —NR'R", —$CF_3$, —CN, —$NO_2$, —$C_2$R', —SR', —$N_3$, —C(=O)NR'R", —NR'C(=O) R", —C(=O)R', —C(=O)OR', —OC(=O)R', —OC(=O)NR'R", —NR'C(=O)O R", —$SO_2$R', —$SO_2$NR'R", or —NR'$SO_2$R", where R' and R" are, individually, hydrogen, $C_{1-6}$ alkyl, cycloalkyl, heterocyclyl, aryl, or arylalkyl.

2. The method of claim 1, wherein the compound is 2-(4-Bromo-phenyl)-4-piperazin-1-yl-quinazoline, wherein any of the aromatic rings in these compounds can be optionally substituted with one or more substituents, Z, wherein Z is defined as $C_{1-6}$ alkyl, alkenyl, heterocyclyl, aryl, heteroaryl, halo —OR', —NR'R", —$CF_3$, —CN, —$NO_2$, —$C_2$R', —SR', —$N_3$, —C(=O)NR'R", —NR'C(=O) R", —C(=O)R', —C(=O)OR', —OC(=O)R', —OC(=O)NR'R", —NR'C(=O)O R", —$SO_2$R', —$SO_2$NR'R", and —NR'$SO_2$R", where R' and R" are individually hydrogen, $C_{1-6}$ alkyl, cycloalkyl, heterocyclyl, aryl, or arylalkyl.

3. The method of claim 1, wherein the compound is 2-(4-bromophenyl)-4-(1-piperazinyl)-quinazoline.

* * * * *